United States Patent
Frank et al.

(10) Patent No.: US 7,799,971 B2
(45) Date of Patent: Sep. 21, 2010

(54) METHOD FOR INCREASING PATHOGEN-RESISTANCE IN TRANSGENIC PLANTS BY EXPRESSION OF PEROXIDASE

(75) Inventors: Markus Frank, Mannheim (DE); Ralf-Michael Schmidt, Kirrweiler (DE); Sandra Stauder, Weisenheim am Berg (DE)

(73) Assignee: BASF Plant Sciences GmbH, Ludwigshafen (DE)

( * ) Notice: Subject to any disclaimer, the term of this patent is extended or adjusted under 35 U.S.C. 154(b) by 384 days.

(21) Appl. No.: 11/630,655

(22) PCT Filed: Jun. 14, 2005

(86) PCT No.: PCT/EP2005/006376

§ 371 (c)(1),
(2), (4) Date: Feb. 20, 2007

(87) PCT Pub. No.: WO2006/000319

PCT Pub. Date: Jan. 5, 2006

(65) Prior Publication Data
US 2008/0282425 A1    Nov. 13, 2008

(30) Foreign Application Priority Data
Jun. 24, 2004    (DE) .................. 10 2004 030 608

(51) Int. Cl.
| | |
|---|---|
| *C12N 15/09* | (2006.01) |
| *C12N 15/29* | (2006.01) |
| *C12N 15/82* | (2006.01) |
| *A01H 5/00* | (2006.01) |
| *A01H 5/10* | (2006.01) |

(52) U.S. Cl. ............... 800/279; 800/278; 800/295; 800/298; 800/287; 800/320; 800/317; 435/320.1; 435/468; 435/430.1; 536/23.6

(58) Field of Classification Search .............. None
See application file for complete search history.

(56) References Cited

FOREIGN PATENT DOCUMENTS

| | | |
|---|---|---|
| EP | 1 249 493 | 10/2002 |
| WO | WO-97/41237 | 11/1997 |
| WO | WO-02/070723 | 9/2002 |
| WO | WO 02/070723 A2 * | 9/2002 |

OTHER PUBLICATIONS

Accession No. AAC49694, deposited Oct. 18, 2001.*
P. Simon, Plant Peroxidase Newsletter, No. 1, pp. 1-6, Feb. 1993.*
Kristensen, B. K., et al., "Expression of a Defence-related Intercellular Barley Peroxidase in Transgenic Tobacco", Plant Science, 1997, vol. 122, pp. 173-182.
Shi, W. M., et al., "Cloning of Peroxisomal Ascorbate Peroxidase Gene From Barley and Enhanced Thermotolerance by Overexpressing in *Arabidopsis thaliana*", Gene, 2001, vol. 273, pp. 23-27.
"HS06P24r HS Hordeum vulgare subsp. vulgare cDNA clone HS06P24 5-PRIME, mRNA sequence", EMBL GenBank Accession No. CA002255, Nov. 8, 2002.
"Peroxidase [*Arabidopsis thaliana*]", NCBI Database Accession No. BAA96930, Feb. 14, 2004.
FGAS028792, Triticum aestivum FGAS: Library 6 CAP GATE 1, Triticum aestivum cDNA, mRNA sequence, GenBank Accessin No. CK216791, Dec. 9, 2003.
FGAS025872, Triticum aestivum FGAS; Library 6 CAP GATE 1, Triticum aestivum cDNA, mRNA sequence, GenBank Accession No. CK213957, Dec. 9, 2003.
"Barley mRNA for Peroxidase (EC=1.11.1.7)", NCBI GenBank, Accession No. X58396, Feb. 15, 1993.

* cited by examiner

*Primary Examiner*—Medina A Ibrahim
(74) *Attorney, Agent, or Firm*—Connolly Bove Lodge & Hutz, LLP

(57) ABSTRACT

The present invention relates to a method for the production of transgenic plants and/or plant cells, respectively, with increased pathogen resistance, characterized in that a DNA sequence, which encodes a protein with the activity of a peroxidase, is inserted into the plant and expressed therein. The invention at hand also relates to the use of nucleic acids encoding a peroxidase for the production of transgenic plants, or plant cells, respectively, with increased pathogen resistance. Further, the invention at hand relates to nucleic acid sequences encoding a peroxidase of barley.

27 Claims, 1 Drawing Sheet

Figure 1:
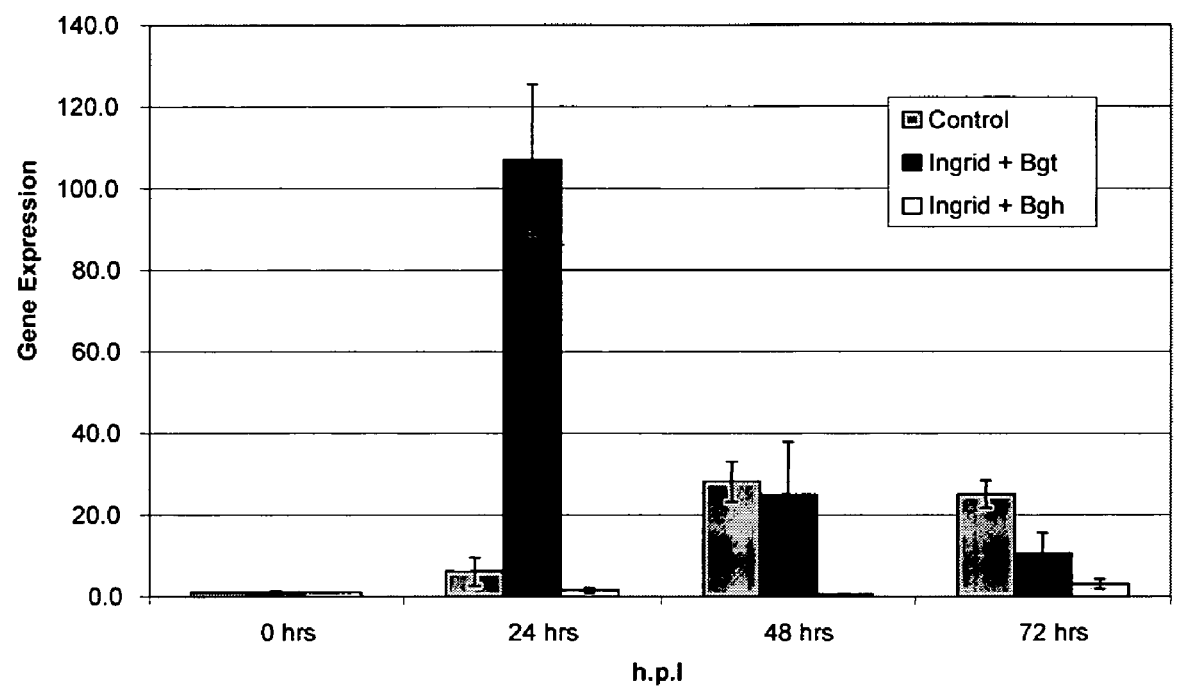

```
                           SEQUENCE LISTING

<160> NUMBER OF SEQ ID NOS: 12

<210> SEQ ID NO 1
<211> LENGTH: 945
<212> TYPE: DNA
<213> ORGANISM: Hordeum vulgare

<400> SEQUENCE: 1
atggcctcta cttcgtccct atcagtggtg ttgctcttgt gcctggccgt ggcggcgtcg      60
gcgcagctgt cgccgacgtt ctaccaaacg acgtgcccga acgctctgtc caccatcaag     120
gccgccgtga cggccgccgt gaacaatgag aaccgcatgg gcgcgtcgct gctccggctg     180
cacttccacg actgcttcgt ccaaggttgt gacgcgtctg ttctgctgtc tggcatggaa     240
caaaacgcgg cgccgaacgt catgtccctg cgaggcttcg aagtcataga cagcatcaag     300
gcgaagctcg agaccatgtg caagcagacc gtctcctgcg ccgacatcct caccgtcgct     360
gcccgcgatt ccgtcgtcgc cttgggaggg ccatcgtgga cggttccgct aggaaggagg     420
gactccacca atgcaaacga agcagcggcg aactccgacc tacctccccc gttcttcgac     480
ctcgtcaacc tcacccaatc cttcggcgac aagggcttca ccgtcaccga catggtcgcg     540
ctctccggtg cccacaccat cggacaggcg cagtgccaga acttcaggga taggctctac     600
aacgagacta acatcaactc cggcttcgcg acgtcgctca aggccaactg cccccggccg     660
accggctccg gcgaccgcaa cctggccaat ctggacgtgt ctaccccgta ctcattcgac     720
aacgcctact acagcaacct caagtcccag aagggggctcc tgcactctga ccaggtgctc     780
ttcaccggca cgggcggcgg cacggacaac atcgtcaaca acttcgcgag caacccagct     840
gcgttcagcg gcgccttttgc ctcggccatg gtgaagatgg ggaacctcag cccattgact     900
ggctctcagg ggcaggtcag gctgagctgc tccaaggtga attaa                      945

<210> SEQ ID NO 2
<211> LENGTH: 314
<212> TYPE: PRT
<213> ORGANISM: Hordeum vulgare

<400> SEQUENCE: 2

Met Ala Ser Thr Ser Ser Leu Ser Val Val Leu Leu Cys Leu Ala
1               5                   10                  15

Val Ala Ala Ser Ala Gln Leu Ser Pro Thr Phe Tyr Gln Thr Thr Cys
            20                  25                  30

Pro Asn Ala Leu Ser Thr Ile Lys Ala Ala Val Thr Ala Ala Val Asn
        35                  40                  45

Asn Glu Asn Arg Met Gly Ala Ser Leu Leu Arg Leu His Phe His Asp
    50                  55                  60

Cys Phe Val Gln Gly Cys Asp Ala Ser Val Leu Leu Ser Gly Met Glu
65                  70                  75                  80

Gln Asn Ala Ala Pro Asn Val Met Ser Leu Arg Gly Phe Glu Val Ile
                85                  90                  95

Asp Ser Ile Lys Ala Lys Leu Glu Thr Met Cys Lys Gln Thr Val Ser
            100                 105                 110
```

```
Cys Ala Asp Ile Leu Thr Val Ala Ala Arg Asp Ser Val Val Ala Leu
            115                 120                 125
Gly Gly Pro Ser Trp Thr Val Pro Leu Gly Arg Arg Asp Ser Thr Asn
        130                 135                 140
Ala Asn Glu Ala Ala Ala Asn Ser Asp Leu Pro Pro Phe Phe Asp
145                 150                 155                 160
Leu Val Asn Leu Thr Gln Ser Phe Gly Asp Lys Gly Phe Thr Val Thr
                165                 170                 175
Asp Met Val Ala Leu Ser Gly Ala His Thr Ile Gly Gln Ala Gln Cys
            180                 185                 190
Gln Asn Phe Arg Asp Arg Leu Tyr Asn Glu Thr Asn Ile Asn Ser Gly
        195                 200                 205
Phe Ala Thr Ser Leu Lys Ala Asn Cys Pro Arg Pro Thr Gly Ser Gly
    210                 215                 220
Asp Arg Asn Leu Ala Asn Leu Asp Val Ser Thr Pro Tyr Ser Phe Asp
225                 230                 235                 240
Asn Ala Tyr Tyr Ser Asn Leu Lys Ser Gln Lys Gly Leu Leu His Ser
                245                 250                 255
Asp Gln Val Leu Phe Thr Gly Thr Gly Gly Thr Asp Asn Ile Val
            260                 265                 270
Asn Asn Phe Ala Ser Asn Pro Ala Ala Phe Ser Gly Ala Phe Ala Ser
        275                 280                 285
Ala Met Val Lys Met Gly Asn Leu Ser Pro Leu Thr Gly Ser Gln Gly
    290                 295                 300
Gln Val Arg Leu Ser Cys Ser Lys Val Asn
305                 310

<210> SEQ ID NO 3
<211> LENGTH: 951
<212> TYPE: DNA
<213> ORGANISM: Arabidopsis thaliana

<400> SEQUENCE: 3
atgttaaagg tggtgttgtt gatgatgata atgatgttgg cgtcacagtc cgaggctcag      60
ctgaaccgtg acttttacaa ggaaagctgt ccatcattgt tccttgtcgt gagacgagtc     120
gtgaaacggg ccgtggccag agagcctcgc atgggtgctt ctctccttcg tttgttcttc     180
catgattgtt ttgtcaatgg gtgtgacgga tccttactgt ggatgacac accgtctttt      240
ttgggagaga aaacctcagg acccagcaat aactctgtga gggggttcga agtgatcgac     300
aaaatcaagt ttaaggttga gaaaatgtgc ccgggcatcg tctcatgcgc agacattcta     360
gccatcactg ctcgggactc cgttctcctc ctaggtggac cggggtggag cgtgaaactt     420
ggaagaagag actctacgac ggcgaacttc gcggccgcga actccggagt catccctcct     480
ccgatcacta cccttagcaa cctcataaac cgtttcaaag cacaaggttt gtccacacgt     540
gacatggtcg ccctctctgg tgctcacacc attggacgag cccaatgtgt acattcaga     600
aaccgaatct acaacgcaag caatatcgac acctctttcg ccatctctaa acggaggaac     660
tgtcctgcca ccagtggctc cggagacaac aagaaagcca atcttgacgt ccgctctccc     720
gataggttcg accacggctt ctacaagcaa cttctgagca aaaaaggttt gcttacgtca     780
gaccaagtcc tcttttaataa tggtcctacc gactcgctcg tcatagctta cagccacaat     840
ctcaatgcct ctaccgcga ctttgcaagg gcaatgatta agatgggaga catcagcccc      900
ctcaccggat ccaatggtca gatccgccaa aactgtcgga ggcccaactg a              951
```

<210> SEQ ID NO 4
<211> LENGTH: 316
<212> TYPE: PRT
<213> ORGANISM: Arabidopsis thaliana

<400> SEQUENCE: 4

```
Met Leu Lys Val Val Leu Leu Met Met Ile Met Met Leu Ala Ser Gln
1               5                   10                  15

Ser Glu Ala Gln Leu Asn Arg Asp Phe Tyr Lys Glu Ser Cys Pro Ser
            20                  25                  30

Leu Phe Leu Val Val Arg Arg Val Val Lys Arg Ala Val Ala Arg Glu
        35                  40                  45

Pro Arg Met Gly Ala Ser Leu Leu Arg Leu Phe Phe His Asp Cys Phe
    50                  55                  60

Val Asn Gly Cys Asp Gly Ser Leu Leu Leu Asp Asp Thr Pro Ser Phe
65                  70                  75                  80

Leu Gly Glu Lys Thr Ser Gly Pro Ser Asn Asn Ser Val Arg Gly Phe
                85                  90                  95

Glu Val Ile Asp Lys Ile Lys Phe Lys Val Glu Lys Met Cys Pro Gly
            100                 105                 110

Ile Val Ser Cys Ala Asp Ile Leu Ala Ile Thr Ala Arg Asp Ser Val
        115                 120                 125

Leu Leu Leu Gly Gly Pro Gly Trp Ser Val Lys Leu Gly Arg Arg Asp
    130                 135                 140

Ser Thr Thr Ala Asn Phe Ala Ala Asn Ser Gly Val Ile Pro Pro
145                 150                 155                 160

Pro Ile Thr Thr Leu Ser Asn Leu Ile Asn Arg Phe Lys Ala Gln Gly
                165                 170                 175

Leu Ser Thr Arg Asp Met Val Ala Leu Ser Gly Ala His Thr Ile Gly
            180                 185                 190

Arg Ala Gln Cys Val Thr Phe Arg Asn Arg Ile Tyr Asn Ala Ser Asn
        195                 200                 205

Ile Asp Thr Ser Phe Ala Ile Ser Lys Arg Arg Asn Cys Pro Ala Thr
    210                 215                 220

Ser Gly Ser Gly Asp Asn Lys Lys Ala Asn Leu Asp Val Arg Ser Pro
225                 230                 235                 240

Asp Arg Phe Asp His Gly Phe Tyr Lys Gln Leu Leu Ser Lys Lys Gly
                245                 250                 255

Leu Leu Thr Ser Asp Gln Val Leu Phe Asn Asn Gly Pro Thr Asp Ser
            260                 265                 270

Leu Val Ile Ala Tyr Ser His Asn Leu Asn Ala Phe Tyr Arg Asp Phe
        275                 280                 285

Ala Arg Ala Met Ile Lys Met Gly Asp Ile Ser Pro Leu Thr Gly Ser
    290                 295                 300

Asn Gly Gln Ile Arg Gln Asn Cys Arg Arg Pro Asn
305                 310                 315
```

<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
agaagtatgt taaaggtggt gttgttg                27

```
<210> SEQ ID NO 6
<211> LENGTH: 23
<212> TYPE: DNA
<213> ORGANISM: Artificial sequence
<220> FEATURE:
<223> OTHER INFORMATION: Primer

<400> SEQUENCE: 6
tgacgaagag gtgattattg agc                                              23

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
cgaggccctt gtgacataca t                                                21

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
acttaggtgt cgttacttgg accat                                            25

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
cgtccctgcc ctttgtacac                                                  20

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
aacacttcac cggaccattc a                                                21

<210> SEQ ID NO 11
<211> LENGTH: 26
<212> TYPE: DNA
<213> ORGANISM: Artificial sequence
<220> FEATURE:
<223> OTHER INFORMATION: Primer

<400> SEQUENCE: 11
gcttattcag cagccaacaa agtaac                                           26

<210> SEQ ID NO 12
<211> LENGTH: 28
<212> TYPE: DNA
<213> ORGANISM: Artificial sequence
<220> FEATURE:
```

-continued

```
<223> OTHER INFORMATION: Primer

<400> SEQUENCE: 12
ctgtttcaca agtttatggt ccaagtaa                                              28
```

METHOD FOR INCREASING PATHOGEN-RESISTANCE IN TRANSGENIC PLANTS BY EXPRESSION OF PEROXIDASE

RELATED APPLICATIONS

This application is a national stage application (under 35 U.S.C. 371) of PCT/EP2005/006376 filed Jun. 14, 2005, which claims benefit to German application 10 2004 030 608.7 filed Jun. 24, 2004.

The present invention relates to a method for the production of transgenic plants and/or plant cells having increased pathogen resistance, characterized in that a DNA sequence, which encodes a protein with the activity of a peroxidase, is inserted into the plant and expressed therein. The present invention also relates to the use of nucleic acids encoding a peroxidase for the production of transgenic plants and/or or plant cells having increased pathogen resistance. Further, the present invention relates to nucleic acid sequences encoding a peroxidase of barley.

Plant diseases caused by various pathogens, such as viruses, bacteria and fungi, can lead to substantial crop losses in the growing of cultivated plants, with economic consequences on the one hand, but also pose a threat for the safety of human food on the other hand. Chemical fungicides have been used since the last century to control fungi diseases. Although the use of these agents led to a reduction in the extent of plant diseases, up to now it cannot be ruled out that these compounds may have harmful effects on humans, animals and the environment. In order to reduce the use of traditional pesticides to a minimum, it is therefore important to examine the natural pathogen defense of various plants to different pathogens, and to make systematic use of genetic engineering, such as by introducing external resistance genes, or by manipulating endogenous gene expression in plants for the production of pathogen resistant plants.

Resistance means the ability of a plant to prevent, or at least curtail the infestation and colonization by a harmful pathogen.

Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and the incompatible interaction. In compatible interaction, an interaction occurs between a virulent pathogen and a susceptible plant. The pathogen survives, and may build up reproduction structures, while the host dies off. An incompatible interaction occurs on the other hand when the pathogen infects the plant but is inhibited in its growth before or after weak development of symptoms. In the latter case, the plant is resistant to the respective pathogen (Schopfer and Brennicke (1999) Pflanzenphysiologie, Springer Verlag, Heidelberg, Germany). In both compatible and incompatible interaction a defensive reaction of the host to the pathogen occurs.

The genetic basis for the compatible or incompatible host/pathogen interaction, respectively, has been described by the gene-for-gene hypothesis (Flor (1971) Annu. Rev. Phytopathology 9: 275 296). A pre-condition for the race specific pathogen recognition is the direct or indirect interaction of the product of a dominant, or semi-dominant resistance gene (R gene) of the plant with a product originating from the complementary and dominant avirulence gene (Avr gene) of the phytopathogen (Keen (1992) Annu. Rev. Genet. 24: 447-463; Staskawicz et al. (1995) Science 268: 661-667). However, if the pathogen is lacking the complementary avirulence gene, the onset of the disease can be the result. The gene-for-gene model has proven true for many rust, smut, powdery as well as downy mildew fungus infections, however, it is not transferable to all host/parasite interactions.

In nature, however, this race specific resistance is often overcome because of the rapid evolutionary development of pathogens (Neu et al. (2003) American Cytopathol. Society, MPMI 16 No. 7: 626-633). As against this, the non-host resistance offers strong, broad, and permanent protection from phytopathogens. Non-host resistance means the phenomenon that a pathogen can induce a disease in a certain plant species, but not in another genetically similar plant species (Heath (2002) Can. J. Plant Pathol. 24: 259-264).

Despite this interesting characteristic, the genetic and molecular biological bases for the non-host resistance have up to now only been poorly understood. There are indications that the non-host resistance is induced by unspecific agents, and also that individual pathogen proteins of the type of the gene-for-gene interaction induce the non-host resistance reaction (Heath (1981) Phytopathology 71: 1121-1123; Heath (2001) Physiol. Mol. Plant. Pathol. 58: 53-54; Kamoun et al. (1998) Plant Cell 10: 1413-1425; Lauge et al. (2000) Plant J. 23: 735-745; Whalen et al. (1988) Proc. Natl. Acad. Sci. USA 85: 6743-6747).

Another reason why the colonization of plants by phytopathogens occurs only rarely is the fact that the pathogen is unable to develop infection structures due to the lack of agents and structures required for the progression of an infection. Furthermore, non-specifically induced or preformed resistance barriers already existing prior to the infection by a pathogen, prevent the formation of infection structures. This resistance is called basic resistance, or race unspecific resistance, and is sustained by means of passive and active defense mechanisms.

The different resistance mechanisms responsible for the resistance or susceptibility of a plant species, or its cultivars to certain plant pathogens will be illustrated by way of example for the mildew fungus (*Blumeria graminis*), which infests several different types of cereals. The mildew fungus is part of the genus *Ascomycetes*, and infests, besides wheat and barley, also rye, oats as well as numerous grasses. The resulting losses in barley and wheat crops can amount to up to 25% in some cases. Usually, however, they are between 5 and 15%. Additionally, the mildew fungus also opens the door to other pathogens (Gray snow mold, Glume blotch, Fusarium head blight etc.). The most prevalent symptom of a mildew infection are the white "mildew pustules" which predominantly occur on the top of the leaf and on the leaf sheaths. Powdery mildew, *Blumeria graminis*, is fastidiously biotrophic, i.e. it can only feed on live substances and cannot be cultivated on a culture medium. Instead, the fungus influences the host metabolism in such a way that its own growth is stimulated (Ferrari et al. (2003) The Plant Journal 35: 193-205). Mildew fungus exclusively infests the epidermal cell layer of barley leaves. The fungus penetrates the plant cell mechanically and enzymatically through the cell wall by means of a penetration peg, which are conidia, i.e. asexually produced spores. The successful infestation of barley leaves is achieved when the haustorium, which is the fungus supply organ, has been formed. The haustoria remove the nutrients from the plant cell, which causes the non-infected, neighboring cells to compensate for this loss of nutrients of the cell, thereby keeping it alive. Through the flow of nutrients into the damaged cell the fungus secures for itself a basis of survival for a certain time.

The mildew fungus as a species comprises several formae speciales depending on whether the respective mildew fungus attacks, e.g. wheat or barley. In the case of an infestation of barley it is called *Blumeria graminis* f. sp. *hordei*, while in the case of an infestation of wheat it is called *Blumeria graminis* f. sp. *tritici*. Furthermore, different races or pathotypes can be identified among the various formae speciales, to which different cultivars of the host species show a different resistance. The formae speciales each attack only a certain plant species and not other, closely related, plants. This is therefore called a non-host resistance of those plants which are not attacked by a certain form a specialis.

Several different genetic mechanisms can be distinguished which provide barley with resistance to mildew. The race specific resistance is based on the resistance genes (R genes) to Barley Powdery Mildew, which is only effective against individual isolates of the fungus *blumeria graminis* f. sp. *hordei*, because each individual R gene, as mentioned above, only recognizes that isolate that carries a complementary avirulence gene (Collins et al. (2002) The Powdery Mildew Accomprehensive Treatise, American Phytopathological Society, Minnesota; Peterhansel et al. (1997) Plant Cell 9: 1397-1409). In contrast, the broad, race unspecific resistance to several mildew isolates is controlled by a single recessive gene which has been called the mlo gene (Schulze-Lefert and Vogel (2000) Trends in Plant Science 5: 343-348). A current hypothesis on the effect of the mlo gene is that the mlo wild type protein is a negative regulator of the defensive reaction, and that the lack of the protein therefore effectuates a quicker and stronger defensive reaction resulting in an effective pathogen defense (Collins et al. (2002), vide supra). The mlo mediated resistance leads to the formation of a subcellular cell wall apposition, called papilla, and which forms directly below the fungus penetration peg, the so-called appressorium. The penetration attempts of the fungus at the stage of papilla formation are thus inhibited, i.e. the haustorium is not formed, which is necessary for the nutrient supply of the fungus and thus for the establishment an efficient infestation.

In contrast to the race-unspecific resistance, defense mechanisms similar to an inoculation of barley with an avirulent form of *blumeria graminis* f. sp. *hordei* (Bgh) are induced in the non-host resistance of barley to the powdery mildew *blumeria graminis* f. sp. *tritici* (Bgt), which attacks wheat, but not barley. Since the non-host resistance is strong, broad and long-lasting, it is of particular interest to identify the genes responsible for the non-host resistance. The non-host resistance of barley could thereby also be agronomically applied for other host/pathogen systems. Therefore, there is a demand for plants, or plant cells, which express genes mediating the non-host resistance, and therefore demonstrate an increased resistance to fungus pathogens, such as mildew.

The object of the present invention is to provide transgenic plants, or plant cells, which have an increased resistance to pathogens. It is further the object of the present invention to provide plants, or plant cells, with a non-host resistance to different pathogens such as mildew. Furthermore, one of the objects of the present invention is to provide methods which facilitate the production of the above-mentioned transgenic plants, or plant cells, having an increased (non-host) resistance to phytopathogens such as mildew.

Furthermore, it is an object of the present invention to provide DNA sequences, with which plants may be identified which have a non-host resistance to pathogens.

The features of the independent claims serve to solve this and further objects shown in the description.

Preferred embodiments of the invention are defined by the features of the sub-claims.

It was found within the scope of the present invention that the interaction of barley with *blumeria graminis* f. sp. *tritici* causes the specific induction of a peroxidase, which is involved in the mediation of the non-host resistance to this form a specialis of mildew.

The stated objects of the present invention are therefore essentially solved by the provision of a method for the production of transgenic plants having increased pathogen resistance, the method being characterized in that a DNA sequence which encodes a protein having the activity of a peroxidase is inserted into the plant and its expressed there.

In the present invention, genes were identified by means of oligonucleotide fingerprinting studies, which were transcriptionally activated through the interaction of barley with bgt compared to the interaction of barley with bgh, and for control purposes. This gene expression pattern was subsequently confirmed by various molecular biological methods, and the full length sequence of the most strongly induced gene was determined. This gene was then identified as a peroxidase and called HvBgt1. The expression of HvBgt1 increases strongly during the non-host reaction of barley with bgt after only 24 hours, whereas during the entire course of the host reaction (barley with bgh) only a slight increase of expression can be observed (compare Table 5 and FIG. 1).

Peroxidase are enzymes through which hydrogen peroxide, as acceptor of molecules of organic compounds, is reduced to water. An important function is attached to peroxidases in the synthesis of the cell wall and the detoxification of xenobiotic substances. Reactive oxygen species are produced during pathogen infection, which may have an adverse effect on the plant. It is assumed that peroxidases enzymatically convert these reactive oxygen species thereby rendering them harmless.

The object of the present invention therefore involves an isolated nucleic acid molecule containing a nucleic acid sequence selected from the group consisting of:

i) DNA sequences comprising nucleotide sequences encoded by SEQ ID No. 1 or fragments of this sequence, ii) DNA sequences comprising nucleotide sequences encoding a protein with the amino acid sequence stated in SEQ ID No. 2 or fragments thereof, iii) DNA sequences, which have a sequence identity of at least 80% with the nucleotide sequence given in SEQ ID No. 1, and/or iv) DNA sequences comprising nucleotide sequences, which hybridize under stringent conditions with a complementary strand of a nucleotide sequence of i) to iii), and which encodes a protein having the activity of a peroxidase.

The nucleic acid sequence is preferably derived from *hordeum vulgare*.

A further object of the present invention concerns proteins or protein fragments which are encoded by the nucleic acid molecules mentioned above.

The object of the present invention also concerns a method for the production of plants, or plant cells, having increased pathogen resistance, characterized in that a DNA sequence is selected from the group consisting of:

i) DNA sequences comprising nucleotide sequences encoded by SEQ ID No. 1, or SEQ ID No. 3, or by fragments of these sequences, ii) DNA sequences comprising nucleotide sequences encoding proteins with the amino acid sequence stated in SEQ ID No. 2, or SEQ ID No. 4, or fragments thereof, iii) DNA sequences, which have a sequence identity of at least 80% with the nucleotide sequence stated in SEQ ID No. 1 or SEQ ID No. 3, and/or iv) DNA sequences comprising nucleotide sequences, which hybridize under stringent conditions with a complementary strand of a nucleotide sequence of i) to iii), which encodes a protein with the activity of a peroxidase, which is inserted into the plant, or plant cell, and is expressed there.

A further object of the present invention concerns recombinant nucleic acid molecules which comprise in 5'-3' orientation:

regulatory sequences of a promoter active in plant cells, operatively linked thereto a nucleic acid sequence as given above, optionally, operatively linked thereto regulatory sequences which may serve as transcription, termination, and/or polyadenylation signals within the plant cell.

The subject-matter of the present invention also involves transgenic plants, or plant cells, produced in accordance with one of the methods according to the invention and which have an increased pathogen resistance and a higher peroxidase content compared to the wild type.

Also subject-matter of the present invention is the use of the nucleic acid sequences described in the invention for the production of transgenic plants and plant cells having increased pathogen resistance.

Further subject-matter of the invention involves the use of one of the nucleic acid sequences described in the invention for the identification of plants showing non-host resistance to pathogens.

"Pathogen resistance" means the lessening or weakening of a plant's pathogenic symptoms following an attack by a pathogen. The symptoms may be of various kinds, but preferably comprise those which directly or indirectly lead to an impairment of the quality of the plant, the size of the harvest, suitability for use as animal fodder or food for human consumption, or which hamper the sowing, cultivation, harvesting or processing of the crop.

According to the invention, the term "increased pathogen resistance" is understood to mean that the transgenic plants, or plant cells according to the invention are less vigorously, and/or less frequently, attacked by pathogens, than non-transformed wild type plants, or plant cells, which were otherwise treated in the same way (such as climate and cultivation conditions, pathogen type, etc.). The infestation with pathogens is preferably reduced by at least a factor of 2, especially preferred by at least a factor of 3, particularly preferred by at least a factor of 5, and most preferred by at least a factor of 10, which is manifested in a reduction of the development of pathogenic symptoms. The penetration efficiency offers one possibility to quantify the pathogen infestation (see example 9). The term "increased pathogen resistance" also comprises what is known as transient pathogen resistance, i.e. the transgenic plants, or plant cells according to the invention have an increased pathogen resistance as compared to the respective wild type only for a limited period of time.

The "pathogens" may be any pathogen which normally attacks the wild type plant, in other words fungal, bacterial, viral and animal pathogens. Preferably, they are fungal pathogens, such as mildew. However, it can also be assumed that the overexpression of a sequence used in accordance with the invention may also create a resistance to further pathogens.

Fungal pathogens, or fungus-like pathogens (such as chromista) are preferably derived from the group comprising plasmodiophoramycota, oomycota, ascomycota, chytridiomycetes, zygomycetes, basidiomycota, and deuteromycetes (fungi imperfecti). The fungal pathogens stated in table 1 and the diseases associated with them are mentioned by way of example, but are not restricted to these.

TABLE 1

Plant fungus diseases

| Disease | Pathogen |
|---|---|
| Brown rust | *Puccinia recondite* |
| Yellow rust | *P. striiformis* |
| Powdery mildew | *Erysiphe graminis/Blumeria graminis* |
| Glume blotch | *Septoria nodorum* |
| Leaf blotch | *Septoria tritici* |
| *Fusarium* head blight | *Fusarium* spp. |
| Eyespot disease | *Pseudocercosporella herpotrichoides* |
| Loose smut | *Ustilago* spp. |
| Wheat bunt | *Tilletia caries* |
| Take-all disease | *Gaeumannomyces graminis* |
| Anthracnose leaf blight | *Colletotrichum graminicola* (telomorphic: |
| Anthracnose stalk rot | *Glomerella graminicola* Politis); *Glomerella tucumanensis* (anamorphic: *Glomerella falcatum* Went) |
| *Aspergillus* ear and kernel rot | *Aspergillus flavus* |
| Banded leaf and sheath spot ("root killer") | *Rhizoctonia solani* Kuhn = *Rhizoctonia microsclerotia* J. Matz (telomorphic: *Thanatephorus cucumeris*) |
| Black bundle disease | *Acremonium strictum* W. Gams = *Cephalosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata*, *C. eragrostidis*, = *C. maculans* (telomorphic: *Cochliobolus eragrostidis*), *Curvularia inaequalis*, *C. intermedia* (telomorphic: *Cochliobolus intermedius*), *curvularia lunata* (telomorphic: *Cochliobolus lunatus*), *Curvularia pallescens* (telomorphic: *Cochliobolus pallescens*), *Curvularia senegalensis*, *C. tuberculata* (telomorphic: *Cochliobolus tuberculatus*) |
| *Didymella* leaf spot | *Didymella exitalis* |
| *Diplodia* ear rot and stalk rot | *Diplodia frumenti* (telomorphic: *Botryosphaeria festucae*) |
| *Diplodia* ear rot, stalk rot, seed rot and seedling blight | *Diplodia maydis* = *Stenocarpella maydis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| Dry ear rot (cob, kernel and stalk rot) | *Nigrospora oryzae* (telomorphic: *Khuskia oryzae*) |

TABLE 1-continued

Plant fungus diseases

| Disease | Pathogen |
|---|---|
| Ear rots, minor | Alternaria alternata = A. tenuis, Aspergillus glaucus, A. niger, Aspergillus spp., Botrytis cinerea (telomorphic: Botryotinia fuckeliana), Cunninghamella sp., Curvularia pallescens, Doratomyces stemonitis = Cephalotrichum stemoniis, Fusarium culmorum, Gonatobotrys simplex, Pithomyces maydicus, Rhizopus microsporus Tiegh., R. stolonifer = R. nigricans, Scopulariopsis brumptii |
| Ergot (horse's tooth) | Claviceps gigantea (anamorphic: sphacelia sp.) |
| Eyespot | Aureobasidium zeae = Kabatiella zeae |
| Fusarium ear and stalk rot | Fusarium subglutinans = F. moniliforme var.subglutinans |
| Fusarium kernel, root and stalk rot, seed rot and seedling blight | Fusarium moniliforme (telomorphic: Gibberella fujikuroi) |
| Fusarium stalk rot, seedling root rot | Fusarium avenaceum (telomorphic: Gibberella avenacea) |
| Gibberella ear and stalk rot | Gibberella zeae (anamorphic: Fusarium graminearum) |
| Gray ear rot | Botryosphaeria zeae = Physalospora zeae (anamorphic: Macrophoma zeae) |
| Gray leaf spot (Cercospora leaf spot) | Cercospora sorghi = C. sorghi var. maydis, C. zeae-maydis |
| Helminthosporium root rot | Exserohilum pedicellatum = Helminthosporium pedicellatum (telomorphic: Setosphaeria pedicellata) |
| Hormodendrum ear rot (Cladosporium rot) | Cladosporium cladosporioides = Hormodendrum cladosporioides, C. herbarum (telomorphic: Mycosphaerella tassiana) |
| Hyalothyridium leaf spot | Hyalothyridium maydis |
| Late wilt | Cephalosporium maydis |
| Leaf spots, minor | Alternaria alternata, Ascochyta maydis, A. tritici, A. zeicola, Bipolaris victoriae = Helminthosporium victoriae (telomorphic: Cochliobolus victoriae), C. sativus (anamorphic: Bipolaris sorokiniana = H. sorokinianum = H. sativum), Epicoccum nigrum, Exserohilum prolatum = Drechslera prolata (telomorphic: Setosphaeria prolata) Graphium penicillioides, Leptosphaeria maydis, Leptothyrium zeae, Ophiosphaerella herpotricha, (anamorphic: Scolecosporiella sp.), Paraphaeosphaeria michotii, Phoma sp., Septoria zeae, S. zeicola, S. zeina |
| Northern corn leaf blight (white blast, crown stalk rot, stripe) | Setosphaeria turcica (anamorphic: Exserohilum turcicum = Helminthosporium turcicum) |
| Northern corn leaf spot Helminthosporium ear rot (race 1) | Cochliobolus carbonum (anamorphic: Bipolaris zeicola = Helminthosporium carbonum) |
| Penicillium ear rot (blue eye, blue mold) | Penicillium spp., P. chrysogenum, P. expansum, P. oxalicum |
| Phaeocytostroma stalk rot and root rot | Phaeocytostroma ambiguum, = Phaeocytosporella zeae |
| Phaeosphaeria leaf spot | Phaeosphaeria maydis = Sphaerulina maydis |
| Physalospora ear rot (Botryosphaeria ear rot) | Botryosphaeria festucae = Physalospora zeicola (anamorphic: Diplodia frumenti) |
| Purple leaf sheath | Hemiparasitic bacteria and fungi |
| Pyrenochaeta stalk rot and root rot | Phoma terrestris = Pyrenochaeta terrestris |
| Pythium root rot | Pythium spp., P. arrhenomanes, P. graminicola |
| Pythium stalk rot | Pythium aphanidermatum = P. butleri L. |
| Red kernel disease (ear mold, leaf and seed rot) | Epicoccum nigrum |
| Rhizoctonia ear rot (sclerotial rot) | Rhizoctonia zeae (telomorphic: Waitea circinata) |
| Rhizoctonia root rot and stalk rot | Rhizoctonia solani, Rhizoctonia zeae |
| Root rots, minor | Alternaria alternata, Cercospora sorghi, Dictochaeta fertilis, Fusarium acuminatum (telomorphic: Gibberella acuminata), F. equiseti (telomorphic: G. intricans), F. oxysporum, F. pallidoroseum, F. poae, F. roseum, G. cyanogena, (anamorphic: F. sulphureum), Microdochium bolleyi, Mucor sp., Periconia circinata, Phytophthora cactorum, P. drechsleri, P. nicotianae var. parasitica, Rhizopus arrhizus |
| Rostratum leaf spot (Helminthosporium leaf disease, ear and stalk rot) | Setosphaeria rostrata, (anamorphic: Exserohilum rostratum = He/minthosporium rostratum) |
| Rust, common corn | Puccinia sorghi |
| Rust, southern corn | Puccinia polysora |
| Rust, tropical corn | Physopella pallescens, P. zeae = Angiopsora zeae |
| Sclerotium ear rot (southern blight) | Sclerotium rolfsii sacc. (telomorphic: Athelia rolfsii) |
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae (anamorphic: F. graminearum), Macrophomina phaseolina, Penicillium spp., Phomopsis sp., Pythium spp., Rhizoctonia solani, R. zeae, Sclerotium rolfsii, Spicaria sp. |
| Selenophoma leaf spot | Selenophoma sp. |
| Sheath rot | Gaeumannomyces graminis |
| Shuck rot | Myrothecium gramineum |
| Silage mold | Monascus purpureus, M rubber |
| Common smut | Ustilago zeae = U. maydis |
| False smut | Ustilaginoidea virens |
| Head smut | Sphacelotheca reiliana = sporisorium holcisorghi |
| Southern corn leaf blight and stalk rot | Cochliobolus heterostrophus (anamorphic: Bipolaris maydis = Helminthosporium maydis) |
| Southern leaf spot | Stenocarpella macrospora = Diplodia macrospora |
| Stalk rots, minor | Cercospora sorghi, Fusarium episphaeria, F. merismoides, F. oxysporum Schlechtend, F. poae, F. roseum, F. solani (telomorphic: Nectria haematococca), F. tricinctum, Mariannaea elegans, Mucor sp., Rhopographus zeae, Spicaria sp. |
| Storage rots | Aspergillus spp., Penicillium spp. and other fungi |
| Tar spot | Phyllachora maydis |
| Trichoderma ear rot and root rot | Trichoderma viride = T. lignorum telomorphic: Hypocrea sp. |
| White ear rot, root and stalk rot | Stenocarpella maydis = Diplodia zeae |
| Yellow leaf blight | Ascochyta ischaemi, Phyllosticta maydis (telomorphic: Mycosphaerella zeae-maydis) |
| Zonate leaf spot | Gloeocercospora sorghi |

Especially preferred, the peroxidase confers resistance against

Plasmodiophoromycota, such as *Plasmodiophora brassicae* (clubroot of crucifers), *Spongospora subterranea* (powdery scab of potato tubers), *Polymyxa graminis* (root disease of cereals and grasses);

Oomycota, such as *Bremia lactucae* (downy mildew of lettuce), *Peronospora* (downy mildew) in snapdragon (*P. antirrhini*), onion (*P. destructor*), spinach (*P. effusa*), soy bean (*P. manchurica*), tobacco ("blue mold"; *P. tabacina*) alfalfa and clover (*P. trifolium*), *Pseudoperonospora humuli* (downy mildew of hop), *Plasmopara* (downy mildew of grapes) (*P. viticola*), and sunflower (*P. halstedii*), *Ssclerophtohra macrospora* (downy mildew of cereals and grasses), *Pythium* (seed rot, seedling damping-off, and root rot and all types of plants, for example, black root of the beetroot by *P. debaryanum*), *Phytophthora infestans* (late blight of potato and tomato, etc.), *Albugo* spec. (white rust of cruciferous plants);

Ascomycota, such as *Microdochium nivale* (snow mold of rye and wheat), *Fusarium graminearum, Fusarium culmorum* (ear rot, especially of wheat), *Fusarium oxysporum* (fusarium wilt of tomato), *Blumeria graminis* (powdery mildew of barley (f.sp. *hordei*) and wheat (f.sp. *tritici*)), *Erysiphe pisi* (powdery mildew of pea), *Nectria galligena* (canker of fruit trees), *Unicnula necator* (powdery mildew of grape vine), *Pseudopeziza tracheiphila* ("Rotbrenner" of the grape vine), *Claviceps purpurea* (ergot of, for example, rye and grasses), *Gaeumannomyces graminis* (Take-all disease of wheat, rye and other grasses), *Magnaporthe grisea* (rice blast disease), *Pyrenophora graminea* (leaf stripe of barley), *Pyrenophora teres* (net blotch of barley), *Pyrenophora tritici-repentis* (tan spot (yellow spot) of wheat), *Venturia inaequalis* (apple scab), *Sclerotinia sclerotium* (white mold), *Pseudopeziza medicaginis* (common leaf spot of alfalfa, white and red clover);

Basidiomycetes, such as *Typhula incarnata* (*typhula blight* (gray snow mold) of barley, rye, wheat), *Ustilago maydis* (corn smut), *Ustilago nuda* (loose smut of barley), *Ustilago tritici* (loose smut of wheat, spelt), *Ustilago avenae* (loose smut of oat), *Rhizoctonia solani* (black scurf of potatoes), *Sphacelotheca* spp. (head smut of sorghum), *Melampsora lini* (rust of flax), *Puccinia graminis* (black stem rust of wheat, barley, rye, oat), *Puccinia recondita* (leaf rust of wheat), *Puccinia dispersa* (leaf rust of rye), *Puccinia hordei* (leaf rust of barley), *Puccinia coronata* (crown rust of oat), *Puccinia striiformis* (yellow rust of wheat, barley, rye, as well as numerous grasses), *Uromyces appendiculatus* (common bean rust), *Sclerotium rolfsii* (root and stem rots of many plants);

Deuteromycetes (fungi imperfecti), such as *Septoria nodorum* (glume blotch) of wheat (*septoria tritici*), *Pseudocercosporella herpotrichoides* (eyespot of wheat, barley, rye), *Rynchosporium secalis* (leaf blotch of rye and barley), *Alternaria solani* (early blight of potato, tomato), *Phoma betae* (black root of the rootbeet), *Cercospora beticola* (leaf spot of rootbeet), *Alternaria brassicae* (crucifer black spot of oilseed rape, cabbage, and other crucifers), *Verticillium dahliae* (wilt and stem rot of oilseed rape), *Colletotrichum lindemuthianum* (bean anthracnose), *Phoma lingam*—black leg (black leg of cabbage; stem canker of oilseed rape), *Botrytis cinerea* (gray mold of grape vine, strawberry, tomato, hop, etc.).

Most preferred, the plants produced by the method according to the invention are resistant to *Phytophthora infestans* (black spot, late blight of tomato, etc.), *Microdochium nivale* (previously known as *Fusarium nivale*; snow mold of rye and wheat), *Fusarium graminearum, Fusarium culmorum* (crown rot of wheat), *Fusarium oxysporum* (fusarium wilt of tomato), *Blumeria graminis* (powdery mildew of barley (f. sp. *hordei*) and of wheat (f. sp. *tritici*)), *Magnaporthe grisea* (rice blast disease), *Sclerotinia sclerotium* (white mold, canker of oilseed rape), *Septoria nodorum* and *Septoria tritici* (glume blotch of wheat), *Alternaria brassicae* (crucifer black spot of oilseed rape, cabbage, and other crucifers), *Phoma lingam* (black leg of cabbage; root neck, stem canker of oilseed rape).

The pathogens listed in Table 2 and the diseases associated with them can be mentioned by way of example for bacterial pathogens, although not restricted to these.

TABLE 2

Bacterial Diseases

| Disease | Pathogen |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Black leg (soft-rot) | *Erwinia carotovora* subsp. *carotovora*, *Erwinia chrysanthemi* pv. *Zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv. and *nebraskense* |
| *Holcus* spot | *Pseudomonas syringae* pv. *syringae* |
| Purple leaf sheath | Hemiparasitic bacteria |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

Especially preferred, the transgenic plants produced according to the invention are resistant to the following pathogenic bacteria:

*Corynebacterium sepedonicum* (bacterial ring rot of potato), *Erwinia carotovora* (black leg of potato), *Erwinia amylovora* (fire blight of pear, apple, quince), *Streptomyces scabies* (potato scab), *Pseudomonas syringae* pv. *tabaci* (wildfire of tobacco), *Pseudomonas syringae* pv. *phaseolicola* (halo blight of bush bean), *Pseudomonas syringae* pv. tomato ("bacterial speck" of tomato), *Xanthomonas campestris* pv. *malvacearum* (bacterial blight of cotton), and *Xanthomonas campestris* pv. *oryzae* (bacterial leaf blight of rice and other grasses).

The term "viral pathogens" includes all plant viruses, such as the tobacco or cucumber mosaic virus, ringspot virus, necrosis virus, maize dwarf mosaic virus, etc.

The pathogens listed in Table 3 and the diseases associated with them can be mentioned by way of example for viral pathogens, although not restricted to these.

TABLE 3

Viral Diseases

| Disease | Pathogen |
|---|---|
| American wheat striate (wheat striate mosaic) | American wheat striate mosaic virus (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle | Cereal chlorotic mottle virus (CCMV) |
| Corn chlorotic vein banding (Brazilian maize mosaic) | Corn chlorotic vein banding virus (CCVBV) |

TABLE 3-continued

Viral Diseases

| Disease | Pathogen |
| --- | --- |
| Corn lethal necrosis | Virus complex of maize chlorotic mottle virus (MCMV), and maize dwarf mosaic virus (MDMV) A or B, or wheat streak mosaic virus(WSMV) |
| Cucumber mosaic | Cucumber mosaic virus (CMV) |
| Cynodon chlorotic streak | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line | Maize line virus (MLV) |
| Maize mosaic (corn leaf stripe, enanismo rayado) | Maize mosaic virus (MMV) |
| Maize mottle and chlorotic stunt | Maize mottle and chlorotic stunt virus |
| Maize pellucid ringspot | Maize pellucid ringspot virus (MPRV) |
| Maize raya gruesa | Maize raya gruesa virus (MRGV) |
| maize rayado fino (fine striping disease) | Maize rayado fino virus (MRFV) |
| Maize red leaf and red stripe | Mollicute |
| Maize red stripe | Maize red stripe virus (MRSV) |
| Maize ring mottle | Maize ring mottle virus (MRMV) |
| Maize rio IV | Maize rio cuarto virus (MRCV) |
| Maize rough dwarf (nanismo ruvido) | Maize rough dwarf virus (MRDV) (Cereal tillering disease virus) |
| Maize sterile stunt | Maize sterile stunt virus (strains of barley yellow striate virus) |
| Maize streak | Maize streak virus (MSV) |
| Maize stripe (maize chlorotic stripe, maize hoja blanca) | Maize stripe virus |
| Maize stunting | Maize stunting virus |
| Maize tassel abortion | Maize tassel abortion virus (MTAV) |
| Maize vein enation | Maize vein enation virus (MVEV) |
| Maize wallaby ear | Maize wallaby ear virus (MWEV) |
| Maize white leaf | Maize white leaf virus |
| Maize white line mosaic | Maize white line mosaic virus (MWLMV) |
| Millet red leaf | Millet red leaf virus (MRLV) |
| Northern cereal mosaic | Northern cereal mosaic virus (NCMV) |
| Oat pseudorosette (zakuklivanie) | Oat pseudorosette virus |
| Oat sterile dwarf | Oat sterile dwarf virus (OSDV) |
| Rice black-streaked dwarf | Rice black-streaked dwarf virus (RBSDV) |
| Rice stripe | Rice stripe virus (RSV) |
| Sorghum mosaic | Sorghum mosaic virus (SrMV) (also: sugarcane mosaic virus (SCMV) strains H, I and M) |
| Sugarcane Fiji disease | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Wheat spot mosaic | Wheat spot mosaic virus (WSMV) |

The peroxidase according to the invention can also confer resistance against animal pests, such as insects and nematodes. Insects such as beetles, caterpillars, lice, or mites can be mentioned by way of example, although not restricted to these.

The peroxidase according to the invention preferably confers resistance against insects of the genera *Coleoptera, Diptera, Hymenoptera, Lepidoptera, Mallophaga, Homoptera, Hemiptera, Orthoptera, Thysanoptera. Dermaptera, Isoptera, Anoplura, Siphonaptera, Trichoptera*, etc. Especially preferred are insects of the genera *Coleoptera* and *Lepidoptera*, such as the European corn borer (ECB), *Diabrotica barberi* (Northern corn rootworm), *Diabrotica undecimpunctata* (Southern corn rootworm), *Diabrotica virgifera* (Western corn rootworm), *Agrotis ipsilon* (black cutworm), *Crymodes devastator* (glassy cutworm), *Feltia ducens* (dingy cutworm), *Agrotis gladiaria* (claybacked cutworm), *Melanotus* spp., *Aeolus mellillus* (wireworm), *Aeolus mancus* (wheat wireworm), *Horistonotus uhlerii* (sand wireworm), *Sphenophorus maidis* (maize billbug), *Sphenophorus zeae* (timothy billbug), *Sphenophorus parvulus* (bluegrass billbug), *Sphenophorus callosus* (Southern corn billbug), *Phyllogphaga* spp.(white grubs), *Anuraphis maidiradicis* (corn root aphid), *Delia platura* (seedcorn maggot), *Colaspis brunnea* (grape colaspis), *Stenolophus lecontei* (seedcorn beetle) und Clivinia impressifrons (lender seedcorn beetle).

Others are the cereal leaf beetle (*Oulema melanopus*), the frit fly (*Oscinella frit*), wireworms (*Agrotis lineatus*) and aphids (such as the oat aphid *Rhopalosiphum padi*, the grain aphid *Sitobion avenae*).

The pathogens and diseases associated with them listed in Table 4 are named by way of example for nematode pests, although not restricted to these.

TABLE 4

Parasite Nematodes

| Damage | Pathogenic Nematodes |
| --- | --- |
| Awl | *Dolichodorus* spp., *D. heterocephalus* |
| Bulb and stem; Europe | *Ditylenchus dipsaci* |
| Burrowing | *Radopholus similis* |
| Cyst | *Heterodera avenae, H. zeae, Punctodera chalcoensis* |
| Dagger | *Xiphinema* spp., *X. americanum, X. mediterraneum* |
| False root-knot | *Nacobbus dorsalis* |
| Lance, Columbia | *Hoplolaimus Columbus* |
| Lance | *Hoplolaimus* spp., *H. galeatus* |
| Lesion | *Pratylenchus* spp., *P. brachyurus, P. crenatus, P. hexincisus, P. neglectus, P. penetrans, P. scribneri, P. thornei, P. zeae* |
| Needle | *Longidorus* spp., *L. breviannulatus* |
| Ring | *Criconemella* spp., *C. Ornata* |
| Root-knot | *Meloidogyne* spp., *M. chitwoodi, M. incognita, M. Javanica* |
| Spiral | *Helicotylenchus* spp. |
| Sting | *Belonolaimus* spp., *B. longicaudatus* |
| Stubby-root | *Paratrichodorus* spp., *P. christiei, P. minor, Quinisulcius acutus, Trichodorus* spp. |
| Stunt | *Tylenchorhynchus dubius* |

The transgenic plants according to the invention are particularly preferably resistant against *Globodera rostochiensis* and *G. pallida* (cyst nematode of the potato, tomato, and other solanaceous herbs), *Heterodera schachtii* (sugar beet cyst nematode of the sugar and fodder beet, oilseed rape, cabbage, etc.), *Heterodera avenae* (cereal cyst nematode of oat and other cereals), *Ditylenchus dipsaci* (stem and bulb nematode, sugar beet head nematode of rye, oat, corn, clover, tobacco, beet), *Anguina tritici* (wheat seed gall nematode, seed and leaf gall of wheat (spelt, rye), *Meloidogyne hapla* (Northern root-knot nematode of the carrot, cucumber, lettuce, tomato, potato, sugar beet, alfalfa).

For particular species which are especially important in agriculture, the peroxidase used according to the invention is preferably effective against the following pathogens:

For barley, against the fungal, bacterial and viral pathogens *Puccinia graminis* f.sp. *hordei* (barley stem rust), *Blumeria* (*Erysiphe*) *graminis* f.sp. *hordei* (barley powdery mildew), barley yellow dwarf virus (BYDV), and the pathogenic insects/nematodes *Ostrinia nubilalis* (European corn borer); *Agrotis ipsilon* (black cutworm); *Schizaphis graminum* (greenbug); *Blissus leucopterus* (chinch bug); *Acrosternum hilare* (green stink bug); *Euschistus servus* (brown stink bug);

*Deliaplatura* (seedcorn maggot); *Mayetiola destructor* (Hessian fly); *Petrobia latens* (brown wheat mite).

For soy bean, against the fungal, bacterial or viral pathogens *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum* dematium (*Colletotrichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffussa*, *Fusarium semitectum*, *Phialophora gregata*, soybean mosaic virus, *Glomerella glycines*, tobacco ring spot virus, tobacco streak virus, *Phakopsora pachyrhizi*, *Pythium aphanidermatum*, *Pythium ultimum*, *Pythium debaryanum*, tomato spotted wilt virus, *Heterodera glycines*, *Fusarium solani*, and the pathogenic insects/nematodes *Pseudoplusia includens* (soy bean looper); *Anticarsia gemmatalis* (velvetbean caterpillar); *Plathypena scabra* (green cloverworm); *Ostrinia nubilalis* (European corn borer); *Agrotis ipsilon* (black cutworm); *Spodoptera exigua* (beet armyworm); *Heliothis virescens* (cotton budworm); *Helicoverpa zea* (cotton bollworm); *Epilachna varivestis* (Mexican bean beetle); *Myzus persicae* (green peach aphid); *Empoasca fabae* (potato leaf hopper); *Acrosternum hilare* (green stink bug); *Melanoplus femurrubrum* (redlegged grasshopper); *Melanoplus differentialis* (differential grasshopper); *Hylemya platura* (seedcorn maggot); *Sericothrips variabilis* (soybean thrips); *Thrips tabaci* (onion thrips); *Tetranychus turkestani* (strawberry spider mite); *Tetranychus urticae* (two-spotted spider mite).

For canola, against the fungal, bacterial, or viral pathogens *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*.

For alfalfa, against the fungal, bacterial, or viral pathogens *Clavibater michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfa*, *Aphanomyces euteiches*, *Stemphylium herbarum*, *Stemphylium alfalfa*.

For wheat, against the fungal, bacterial or viral pathogens *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium* aphanidermatum, *Pythium arrhenomanes*, *Pythium ultimum*, *Bipolaris* sorokiniana, barley yellow dwarf virus, brome mosaic virus, soil borne wheat mosaic virus, wheat streak mosaic virus, wheat spindle streak virus, American wheat striate virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus, *Puccinia graminis* f.sp. *tritici* (wheat stem rust), Blumeria (Erysiphe) *graminis* f.sp. *tritici* (wheat powdery mildew), and the pathogenic insects/nematodes *Pseudaletia unipunctata* (army worm); *Spodoptera frugiperda* (fall armyworm); *Elasmopalpus lignosellus* (lesser cornstalk borer); *Agrotis orthogonia* (Western cutworm); *Elasmopalpus Zignosellus* (lesser cornstalk borer); *Oulema melanopus* (cereal leaf beetle); *Hypera punctata* (clover leaf weevil); *Diabrotica undecimpunctata howardi* (Southern corn rootworm); Russian wheat aphid; *Schizaphis graminum* (greenbug); *Macrosiphum avenae* (English grain aphid); *Melanoplus femurrubrum* (redlegged grasshopper); *Melanoplus differentialis* (differential grasshopper); *Melanoplus sanguinipes* (migratory grasshopper); *Mayetiola destructor* (Hessian fly); *Sitodiplosis mosellana* (wheat midge); *Meromyza americana* (wheat stem maggot); *Hylemya coarctata* (wheat bulb fly); *Frankliniella fusca* (tobacco thrips); *Cephus cinctus* (wheat stem sawfly); *Aceria tulipae* (wheat curl mite).

For sunflower, against the fungal, bacterial, or viral pathogens *Plasmophora halstedii*, *Sclerotinia sclerotiorum*, aster yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* p.v. *Carotovora*, *Cephalosporium acremonium*, *Phytophthora cryptogea*, *Albugo tragopogonis*, and the pathogenic insects/nematodes *Suleima helianthana* (sunflower bud moth); *Homoeosoma electellum* (sunflower moth); *zygogramma exclamationis* (sunflower beetle); *Bothyrus gibbosus* (carrot beetle); *Neolasioptera murtfeldtiana* (sunflower seed midge).

For corn, against the fungal, bacterial, or viral pathogens *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* 0, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganese* subsp. *nebraskense*, *Trichoderma viride*, maize dwarf mosaic virus A & B, wheat streak mosaic virus, maize chlorotic dwarf virus, *Claviceps sorghi*, *Pseudonomas avenae*, *Erwinia chrysanthemi* p.v. *Zea*, *Erwinia corotovora*, Cornstunt spiroplasma, *Diplodia macrospora*, *Sclerophthora macrospora*, *Peronosclerospora sorghi*, *Peronosclerospora philippinesis*, *Peronosclerospora maydis*, *Peronosclerospora sacchari*, *Spacelotheca reiliana*, *Physopella zeae*, *Cephalosporium maydis*, *Caphalosporium acremonium*, maize chlorotic mottle virus, High Plains virus, maize mosaic virus, maize Rayado Fino virus, maize streak virus (MSV), maize stripe virus, maize rough dwarf virus, and the pathogenic insects/nematodes *Ostrinia nubilalis* (European corn borer); *Agrotis ipsilon* (black cutworm); *Helicoverpa zea* (corn earworm); *Spodoptera frugiperda*. (fall armyworm); *Diatraea grandiosella* (Southwestern corn borer); *Elasmopalpus lignosellus* (lesser cornstalk borer); *Diatraea saccharalis* (surgarcane borer); *Diabrotica virgifera* (Western corn rootworm); *Diabrotica longicornis* barberi (Northern corn rootworm); *Diabrotica undecimpunctata* howardi (Southern corn rootworm); *Melanotus* spp. (wireworms); *Cyclocephala* borealis (Northern masked chafer; white grub); *Cyclocephala immaculata* (Southern masked chafer; white grub); *Popillia japonica* (Japanese beetle); *Chaetocnema pulicaria* (corn flea beetle); *Sphenophorus maidis* (maize billbug); *Rhopalosiphum maidis* (corn leaf aphid); *Anuraphis maidiradicis* (corn root aphid); *Blissus leucopterus leucopterus* (chinch bug); *Melanoplus femurrubrum* (redlegged grasshopper); *Melanoplus sanguinipes* (migratory grasshopper); *Hylemva platura* (seedcorn maggot); *Agromyza parvicornis* (corn blot leafminer); *Anaphothrips obscrurus* (grass thrips); *Solenopsis milesta* (thief ant); *Tetranychus urticae* (two-spotted spider mite).

For sorghum, against the fungal, bacterial, or viral pathogens *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, maize dwarf mosaic virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* and the pathogenic insects/nematodes *Chilo partellus* (sorghum borer); *Spodoptera frugiperda* (fall armyworm); *Helicoverpa zea* (corn ear-worm); *Elasmopalpus lignosellus* (lesser cornstalk borer); *Feltia subterranea* (granulate cutworm); *Phyllophaga crinita* (white grub); *Eleodes, Conoderus* und *Aeolus* spp. (wireworm); *Oulema melanopus* (cereal leaf beetle); *Chaetocnema pulicaria* (corn flea beetle); *Sphenophorus maidis* (maize billbug); *Rhopalosiphum maidis* (corn leaf aphid); *Siphaflava* (yellow sugarcane aphid); *Blissus leucopterus leucopterus* (chinch bug); *Contarinia sorghicola* (sorghummidge); *Tetranychus cinnabarinus* (carmine spider mite); *Tetranychus urticae* (two-spotted spider mite).

For cotton, against the pathogenic insects/nematodes: *Heliothis virescens* (cotton budworm); *Helicoverpa zea* (cotton bollworm); *Spodoptera exigua* (beet armyworm); *Pectinophora gossypiella* (pink bollworm); *Anthonomus grandis grandis* (boll weevil); *Aphis gossypii* (cotton aphid); *Pseudatomoscelis seriatus* (cotton fleahopper); *Trialeurodes abutilonea* (bandedwinged whitefly); *Lygus lineolaris* (tarnished plant bug); *Melanoplus femurrubrum* (redlegged grasshopper); *Melanoplus differentialis* (differential grasshopper); *Thrips tabaci* (onion thrips); *Franklinkiella fusca* (tobacco thrips); *Tetranychus cinnabarinus* (carmine spider mite); *Tetranychus urticae* (two-spotted spider mite);

For rice, against the pathogenic insects/nematodes *Diatraea saccharalis* (sugarcane borer); *Spodoptera frugiperda* (fall armyworm); *Helicoverpa zea* (corn earworm); *Colaspis brunnea* (grape *colaspis*); *Lissorhoptrus oryzophilus* (rice water weevil); *Sitophilus oryzae* (rice weevil); *Nephotettix nigropictus* (rice leafhopper); *Blissus leucopterus* leucopterus (chinch bug); *Acrosternum hilare* (green stink bug);

For oilseed rape, against the pathogenic insects/nematodes *Brevicoryne brassicae* (cabbage aphid); *Phyilotreta cruciferae* (flea beetle); *Mamestra conjgurata* (Bertha armyworm); *Plutella xylostella* (diamond-back moth); *Delia* ssp. (root maggots).

According to the invention, the term "wild type" is to be understood as the respective non genetically modified parent organism.

The method according to the invention causes an increase of the peroxidase content in a transgenic plant and/or in a plant cell. This increase in content is at least 5%, preferably at least 20%, also preferably at least 50%, especially preferably at least 100%, also especially preferably at least by the factor of 5, particularly preferably at least by the factor of 10, also particularly preferably at least by the factor of 50, and most preferably by the factor of 100."

The term "fragments of DNA," as it is used herein, is to be understood as DNA segments encoding a protein having the activity of a peroxidase, wherein the proteins encoded by the DNA segments essentially have the same peroxidase activity as the proteins encoded by the complete DNA sequence, and the increase of pathogen resistance in transgenic plants according to the invention can be achieved with these fragments.

The term "fragments of the protein," as it is used herein, indicates protein segments having the activity of a peroxidase, wherein the protein segments essentially have the same peroxidase activity as the full length protein, and the increase of the pathogen resistance in transgenic plants according to the invention can be achieved with these fragments.

Essentially the same enzymatic activity of the peroxidase used in the method according to the invention means that the enzymatic activity as compared to the enzymes encoded by the sequence with SEQ ID No. 1, or SEQ ID No. 3, and their derivatives, is still at least 50%, preferably at least 60%, especially preferably at least 70%, and particularly preferably at least 80%, and most preferably at least 90%. Peroxidasis with essentially the same enzymatic activity are thus also capable of producing an increased pathogen resistance in transgenic plants.

The activity of peroxidases can be determined by simple methods known to the person skilled in the art, such as the widely used guajacol peroxidase activity assay (Chance und Maehley (1955) Method Enzymol. 11: 764-775), or the syringaldazine activity assay (Pandolfini et al. (1992) Plant Cell Environ. 15: 719-725).

The term "nucleic acid (molecule)", as it is used herein, comprises furthermore in a preferred embodiment the untranslated sequence located at the 3' and at the 5' end of the encoding gene region: at least 500, preferably 200, especially preferably 100 nucleotides of the sequence upstream of the 5' end of the encoding region, and at least 100, preferably 50, especially preferably 20 nucleotides of the sequence downstream of the 3' end of the encoding gene region. An "isolated" nucleic acid molecule is separated from other nucleic acid molecules present in the natural repository of nucleic acids. An "isolated" nucleic acid preferably has no sequences naturally flanking the nucleic acid in the genomic DNA of the organism from which the nucleic acid originates (e.g. sequences located at the 5' and 3' ends of the nucleic acid). In various embodiments the isolated peroxidase molecule can contain, for example, less than approximately 5 kb, 4 kb, 3 kb, 2 kb, 1 kb, 0.5 kb, or 0.1 kb of nucleotide sequences which naturally flank the nucleic acid molecule in the genomic DNA of the cell from which the nucleic acid originates. All nucleic acid molecules mentioned herein can be e.g. RNA, DNA, or cDNA.

The nucleic acid molecules used in the method, such as a nucleic acid molecule with a nucleotide sequence of SEQ ID No. 1 or SEQ ID No. 3 or a part thereof, can be isolated using standard molecular biological techniques and the sequence information provided herein. With the aid of comparison algorithms, which can be found e.g. on the NCBI homepage, a homologous sequence, for example, or homologous, conserved sequence regions can also be identified on DNA or amino acid level. Essential parts of this sequence, or the entire homologous sequence can be used as a hybridization probe using standard hybridization techniques (as described in Sambrook et al., vide supra) for isolating additional nucleic acid sequences from other organisms which are useful in the method by means of screening of cDNA and/or genomic libraries. Moreover, a nucleic acid molecule comprising a complete sequence of SEQ ID No. 1 or SEQ ID No. 3 or a part thereof, can be isolated by means of a polymerase chain reaction, using oligonucleotide primers on the basis of the sequences given herein or parts thereof (e.g. a nucleic acid molecule comprising the complete sequence or a part thereof can be isolated by means of polymerase chain reaction using oligonucleotide primers which have been generated based on this same sequence). For example, mRNA can be isolated from cells (e.g. by means of the guanidinium thiocyanate extraction method of Chirgwin et al. (1979) Biochemistry 18: 5294—5299), and cDNA can be produced from it by means of reverse transcriptase (e.g. Moloney-MLV reverse transcriptase, available from Gibco/BRL, Bethesda, Md., or AMV reverse transcriptase, available from Seikagaku Amerika, Inc., St. Petersburg, Fla.). Synthetic oligonucleotide primers for amplification by means of polymerase chain reaction can be generated based on one of the sequences shown in SEQ ID No. 1 or SEQ ID No. 3, or with the aid of the amino acid sequences shown in SEQ ID No. 2 or SEQ ID No. 4. A nucleic acid according to the invention can be amplified by using cDNA, or alternatively by using genomic DNA as a template, as well as suitable oligonucleotide primers by means of standard PCR amplification techniques. The nucleic acid amplified in this way can be cloned in a suitable vector and characterized by means of DNA sequence analysis. Oligonucleotides corresponding to a peroxidase nucleotide sequence can be produced by standard synthesis methods, such as an automatic DNA synthesizer. The peroxidase activity of the proteins encoded by these nucleic acid sequences can then be determined by the enzyme assays described above. Using the methods described herein, plants which show a non-host resistance can also be identified by detecting the presence of the peroxidase identified according to the invention.

In the context of this invention the term "hybridization under stringent conditions" means that the hybridization is performed in vitro under conditions stringent enough to ensure a specific hybridization. Stringent in vitro hybridization conditions are known to the person skilled in the art, and can be found in the literature (e.g. Sambrook and Russell (2001) Molecular Cloning: A Laboratory Manual, 3$^{rd}$ edition, Cold Spring Harbour Laboratory Press, Cold Spring Harbour, N.Y.). The term "specific hybridization" refers to the fact that a molecule preferably binds to a certain nucleic acid sequence, the target sequence, under stringent conditions, if the target sequence is part of a complex mixture of, for example, DNA or RNA molecules, but does not bind, or at least to a considerably lesser degree, to other sequences.

Stringent conditions depend on the conditions. Longer sequences hybridize specifically at higher temperatures. In general, stringent conditions are selected so that the hybridization temperature is approximately 5° C. below the melting point ($T_m$) for the specific sequence at a defined ionic strength and a defined pH value. $T_m$ is the temperature (at a defined pH value, a defined ionic strength and a defined nucleic acid concentration) at which 50% of the molecules complementary to the target sequence hybridize to the target sequence in the equilibrium state. Typically, stringent conditions are those in which the salt concentration is at least about 0.01 to 1.0 M of sodium ion concentration (or the concentration of another salt) at a pH of between 7.0 and 8.3 and the temperature is at least 30° C. for short molecules (i.e. for example 10 to 50 nucleotides). Furthermore, stringent conditions can comprise the addition of agents, such as formamide, which destabilizes the hybrids. In hybridization under stringent conditions as used herein, nucleotide sequences which are at least 60% homologous to each other usually remain hybridized to each other. Preferably, the stringent conditions are selected in such a way that sequences which are homologous to each other by at least about 65%, preferably at least about 70%, and especially preferably at least about 75%, or more, usually remain hybridized to each other. A preferred, non-limiting example for stringent hybridization conditions are hybridizations in 6× sodium chloride/sodium citrate (SSC) at about 45° C., followed by one or more washing steps in 0.2×SSC, 0.1% SDS at 50 to 65° C. The temperature ranges, for example, under standard hybridization conditions depending on the type of nucleic acid, between 42° C. and 58° C. in an aqueous buffer at a concentration of 0.1 to 5×SSC (pH 7.2).

If an organic solvent, e.g. 50% formamide, is present in the above-mentioned buffer, the temperature under standard conditions is about 42° C. Preferably, the hybridization conditions for DNA:DNA hybrids are for example 0.1×SSC and 20° C. to 45° C., preferably 30° C. to 45° C. Preferably, the hybridization conditions for DNA:RNA hybrids are for example 0.1×SSC and 30° C. to 55° C., preferably between 45° C. to 55° C. The hybridization temperatures mentioned above are determined for example for a nucleic acid having a length of about 100 base pairs and a G/C content of 50% in the absence of formamide. The person skilled in the art knows how the required hybridization conditions can be determined using the above mentioned, or the following, textbooks: Current Protocols in Molecular Biology, John Wiley & Sons, N.Y. (1989), Hames und Higgins (publisher) 1985, Nucleic Acids Hybridization: A Practical Approach, IRL Press at Oxford University Press, Oxford; Brown (publisher) 1991, Essential Molecular Biology: A Practical Approach, IRL Press at Oxford University Press, Oxford.

The term "sequence identity" in terms of the invention denotes identity, i.e. the same nucleotides in the same 5'-3' sequence, across the entire sequence of the nucleic acid sequence stated in SEQ ID No. 1 or SEQ ID No. 3, of at least 80%, preferably of at least 85%, especially preferred of at least 90%, and most preferred of at least 95%.

The sequence identity is determined by means of a number of programs which are based on various algorithms. The algorithms of Needleman and Wunsch, or of Smith and Waterman, provide particularly reliable results. For the sequence comparisons, the program PileUp (Feng and Doolittle (1987) J. Mol. Evolution. 25: 351-360; Higgins et al. (1989) CABIOS 5: 151-153), or the programs Gap and Best Fit (Needleman and Wunsch (1970) J. Mol. Biol. 48: 443-453, and Smith and Waterman (1981) Adv. Appl. Math. 2: 482-489) were used, which are contained in the GCG software package (Genetics Computer Group, 575 Science Drive, Madison, Wis., USA).

The sequence identity values stated above in percent were determined using the program GAP across the entire sequence region with the following settings: gap weight: 50, length weight: 3, average match: 10,000 and average mismatch: 0.000.

Unless stated otherwise, these settings were used as the standard settings for sequence comparisons.

Nucleic acid sequences deviating from the nucleic acid sequences given in SEQ ID No.1 and SEQ ID No.3 can, for example, be created by the insertion of one or several nucleotide substitutions, additions, or deletions in a nucleotide sequence of SEQ ID No. 1, and SEQ ID No. 3, so that proteins are created into which one or more amino acid substitutions, additions, or deletions were inserted as compared to the sequences stated in SEQ ID No. 2 or SEQ ID No. 4. Mutations can be inserted in one of the sequences of SEQ ID No. 1 and SEQ ID No. 3 using standard techniques, such as site specific mutagenesis and PCR-mediated mutagenesis. Preferably, conservative amino acid substitutions are generated at one or several of the predicted nonessential amino acid residues, that is at amino acid residues which do not influence the enzymatic activity of the peroxidase. In a "conservative amino acid substitution" an amino acid residue is replaced with an amino acid residue having a similar side chain. Families of amino acid residues having similar side chains have been defined in the area of expertise. These families comprise amino acids having basic side chains (such as lysine, arginine, histidine), acidic side chains (such as aspartic acid and glutamic acid), uncharged polar side chains (such as glycine, asparagine, glutamine, serine, threonine, tyrosine, cysteine), nonpolar side chains (such as alanine, valine, leucine, isoleucine, proline, phenylalanine, methionine, tryptophan), beta-branched side chains (such as threonine, valine, isoleucine) and aromatic side chains (such as tyrosine, phenylalanine, tryptophan). A predicted nonessential amino acid residue in the peroxidase used according to the invention will thus preferably be replaced by another amino acid residue from the same family of side chains. Alternatively, in another embodiment the mutations may be inserted randomly across the entire sequence or a part of it encoding the peroxidase, for example, by means of saturation mutagenesis, and the resulting mutants may be screened for the peroxidase activity by recombinantly expressing the encoded protein, in order to identify mutants which have retained the peroxidase activity. The peroxidase activity of the protein can, for example, be determined using the assays described herein.

In terms of the invention, "transgenic" or "recombinant" means, with regard to e.g. a nucleic acid sequence, an expression cassette (=gene construct), or a vector containing the nucleic acid sequence according to the invention, or an organism transformed with the respective nucleic acid sequences, expression cassettes, or vectors, all of those constructs being produced by means of genetic technologies, in which either
a) the nucleic acid sequence according to the invention, or
b) a genetic control sequence functionally linked to the nucleic acid sequence according to the invention, such as a promoter, or
c) a) and b)

is not in its natural genetic environment, or has been modified by genetic techniques, the modification being, for example, a substitution, addition, deletion, inversion, or insertion of one or several nucleotide residues. Natural genetic environment means the natural genomic, or chromosomal locus in the parental organism, or the existence in a genomic library. In case the of a genomic library, the natural genetic environment of the nucleic acid sequence is preferably conserved at least partially. The environment flanks the nucleic acid sequence at least on one side, and has a sequence length of at least 50 bp, preferably at least 500 bp, especially preferably at least 1000 bp, particularly preferably at least 5000 bp. A naturally occurring expression cassette—such as the naturally occurring combination of the natural promoter of the peroxidase with the respective peroxidase genes—becomes a transgenic expression cassette when it is modified by means of non-natural, synthetic ("artificial") methods, such as a mutagenization. Corresponding methods are described in U.S. Pat. No. 5,565,350 or WO 00/15815, for example.

In terms of the invention, the term transgenic plant, or plant cell, means, as described above, that the nucleic acids used in the method are not at their natural site in the genome of the plant, or the plant cell, whereby the nucleic acids can be homologously or heterologously expressed. However, transgenic also means that although the nucleic acids according to the invention are located at their natural site in the genome of an organism, the sequence has been changed as against the natural sequence, and/or the regulatory sequences of the natural sequences have been modified. Preferably, transgenic is to be understood as the expression of the nucleic acids according to the invention at a non-natural site in the genome, i.e. the nucleic acids are homologously, or preferably heterologously expressed.

It is obvious to the person skilled in the art that the nucleic acid sequence used for the production of the transgenic plant, or plant cell, which encodes a peroxidase, may have to be adjusted to the organism specific codon usage. The codon usage can be determined with computer analyses of other known genes of the selected organism.

In a preferred method for the production of transgenic plants, or plant cells, according to the invention having increased pathogen resistance, a nucleic acid sequence encoding a peroxidase according to the invention is transferred to a plant, or plant cell, respectively. This transfer leads to an increase in the expression, or the activity, of the peroxidase, as compared to the wild type plant, or wild type plant cell, and correspondingly to an increase in pathogen resistance in the transgenic plants, or plant cells.

Such a method typically comprises, according to the invention, the following steps:
a) production of a vector comprising the following nucleic acid sequences in the 5'-3' orientation:
   regulatory sequences of a promoter which is active in plant cells,
   operatively linked thereto a DNA sequence encoding a peroxidase, or parts of a peroxidase according to the invention,
   operatively linked thereto regulatory sequences which may serve in the plant cell as transcription, termination, and/or polyadenylation signals,
b) Transfer of the vector from step a) to a plant cell, and optionally, integration into the plant genome; and
c) optionally, regeneration of intact plants from the transformed plant cells.

After their insertion into a plant cell, or plant, the nucleic acids used in the method can either be located on a separate plasmid, or advantageously be integrated into the genome of the host cell. In the case of integration into the genome, the integration can occur randomly, or by means of such a recombination that the native gene is replaced by the inserted copy, which causes the modulation of cellular peroxidase expression, or by using a gene in trans so that the gene is functionally linked to a functional expression unit which contains at least one sequence ensuring the expression of a gene, and at least one sequence ensuring the polyadenylation of a functionally transcribed gene.

According to the invention, an increase in gene expression of a nucleic acid encoding a peroxidase also means the manipulation of the expression of the plant's endogenous peroxidase. This can be achieved, for example, by modifying the promoter DNA sequence for peroxidase encoding genes. Such a modification, which results in a modified, preferably increased expression rate of the endogenous peroxidase gene, can occur by means of deletion or insertion of DNA sequences. Modification of the promoter sequence of endogenous peroxidase genes usually leads to modification of the expressed amount of the peroxidase gene, and thus also to modification of the peroxidase activity detectable in the cell, or the plants.

Another possibility to increase the activity and the content of the endogenous peroxidase is to upregulate the transcription factors involved in the transcription of the endogenous peroxidase gene, for instance by overexpression. The procedures for the overexpression of transcription factors are known to the person skilled in the art, and are also disclosed in the present invention for peroxidases.

Furthermore, increased expression of an endogenous peroxidase gene can be achieved in that a regulator protein, which is not present in the non-transformed organism, interacts with the promoter of these genes. Such a regulator may be a chimeric protein consisting of a DNA binding domain and of a transcription activation domain, described for example in WO 96/06166.

In addition to the nucleic acid sequence for the peroxidase to be transferred, the recombinant nucleic acid molecules which are used for the expression of the peroxidase comprise further regulatory elements. Which precise regulatory elements these vectors have to contain depends in each case on the process in which these vectors are to be used. The person skilled in the art and familiar with the various methods mentioned above for the production of transgenic plants in which the expression of a protein is increased, knows which regulatory and other elements these vectors must contain.

Typically, the regulatory elements which are part of the vectors are such that allow for the transcription and, if desired, for the translation in the plant cell. Depending on the plant selected, this can mean, for example, that that the gene is only expressed and/or overexpressed after induction, or that it is expressed and/or overexpressed immediately. For example, these regulatory sequences are sequences to which inductors or repressors bind, thereby regulating the expression of the nucleic acid. In addition to these new regulatory sequences, or instead of these sequences, the natural regulation of the sequences upstream of the actual structural genes may still be existent, and may possibly have been genetically modified so that the natural regulation is disabled, and the expression of the genes is increased. The recombinant nucleic acid molecule, however, can also be constructed in a simpler manner, i.e. no additional regulation signals are inserted upstream of the nucleic acid sequence, and the natural promoter with its regulation has not been removed. Instead, the natural regulatory sequence has been mutated in such a manner that regulation no longer occurs, and/or gene expression is increased. To increase the activity, these altered promoters can also be inserted singly, in the form of partial sequences, upstream of the natural gene. Furthermore, the gene construct can also advantageously contain one or more so-called enhancer sequences which are functionally linked to the promoter, and which allow an increased expression of the nucleic acid sequence. Additional useful sequences, such as additional regulatory elements or terminators, can also be inserted at the 3' end of the DNA sequences.

In principle, it is possible to use any of the natural promoters with their regulation sequences for the method according to the invention. However, it is also possible and advantageous to use synthetic promoters only or in addition.

The promoters can be either constitutive, inducible, tissue-specific or development-specific promoters. The choice of promoter, as well as of other regulatory sequences, determines the regional and temporal expression pattern, and therefore also the expression of the peroxidase in transgenic plants.

Constitutive promoters include, for example, the core promoter of the Rsyn7 promoter as well as other constitutive promoters described in WO 99/43838 and U.S. Pat. No. 6,072,050; the CaMV 35S promoter (Odell et al. (1985) Nature 313: 810-812); the actin promoter (McElroy et al. (1990) Plant Cell 2:163-171); the ubiquitin promoter (Christensen et al. (1989) Plant Mol. Biol. 12: 619-632 and Christensen et al. (1992) Plant Mol. Biol. 18: 675-689); the pEMU promoter (Last et al. (1991) Theor. Appl. Genet. 81: 581-588); the MAS promoter (Velten et al. (1984) EMBO J. 3: 2723-2730); the ALS promoter (U.S. application Ser. No. 08/409,297), and similar promoters. When using a constitutive promoter, a cell-specific or tissue-specific expression can also be achieved by inhibiting the gene expression in the cells, or tissues, in which they are not desired, e.g. by forming antibodies which bind the gene product and thus prevent its activity, or by suitable inhibitors which act in these cells.

Preferably, the peroxidase gene is expressed by an inducible promoter, and especially preferably by a pathogen-inducible promoter. Such promoters include those of pathogen-related proteins (PR proteins) which are induced after the infection with a pathogen, such as PR proteins, SAR proteins, beta-1,3 glucanase, chitinase, etc. (see, for example, Redolfi et al. (1983) Neth. J. Plant Pathol. 89: 245-254; Uknes et al. (1992) Plant Cell 4: 645-656; and Van Loon (1985) Plant Mol. Virol. 4: 111-116).

Also of particular interest are promoters which are expressed locally at or near the site of pathogen infection, such as those described by Marineau et al. (1987) Plant Mol. Biol. 9: 335-342; Matton et al. (1989) Molecular Plant-Microbe Interactions 2: 325-331; Somsisch et al. (1986) Proc. Natl. Acad. Sci. USA 83: 2427-2430; Somsisch et al. (1988) Mol. Gen. Genet. 2: 93-98; Yang (1996) Proc. Natl. Acad. Sci. USA 93: 14972-14977; Chen et al. (1996) Plant J. 10: 955-966; Zhang et al. (1994) Proc. Natl. Acad. Sci. USA 91: 2507-2511; Warner et al. (1993) Plant J. 3: 191-201; Siebertz et al. (1989) Plant Cell 1: 961-968.

Furthermore, wound-inducible promoters are also preferred for use in the method according to the present invention, since pathogens often enter through wounds. Such wound-inducible promoters include that of the proteinase inhibitor (pin II) of the potato (Ryan (1990) Ann. Rev. Phytopathol. 28: 425-449; Duan et al. (1996) Nature Biotechnology 14: 494-498); wun1 and wun2 (U.S. Pat. No. 5,428,148); win1 and win2 (Stanford et al. (1989) Mol. Gen. Genet. 215: 200-208); Systemin (McGurl et al. (1992) Science 225: 1570-1573); WIPI (Rohmeier et al. (1993) Plant Mol. Biol. 22: 783-792; Eckelkamp et al. (1993) FEBS Letters 323: 73-76); of the MPI gene (Corderok et al. (1994) Plant J. 6 (2): 141-150); the FGAM-Synthase (Vaghchhipawala et al. (2004) Genome 47 (2): 404-413; prxC2 (Kaothien et al. (2002) Plant Mol. Biol. 49 (6): 591-599); poxA (Ito et al. (2000) Plant Science 155 (1): 85-100); FAD7 (Nishiuchi et al. (1999) Plant Physiol. 121 (4): 1239-1246); TR2' (WO 03/093483).

Chemically regulated promoters can be used in order to regulate the expression of a gene in a plant by the use of an exogenous chemical regulator (see review in Gatz (1997) Annu. Rev. Plant Physiol. Plant Mol. Biol., 48: 89-108). Chemically inducible promoters are particularly suited whenever it is desired that the gene expression occurs in a time specific manner. Examples for this include the In2-2 promoter of corn, which is activated by benzenesulfonamide, the GST promoter of corn, which is induced by hydrophobic electrophilic compounds, and the PR-1a promoter of tobacco, which is activated by salicylic acid. Other chemically regulated promoters include steroid responsive promoters (see, for example, the glucocorticoid-inducible promoter in Schena et al. (1991) Proc. Natl. Acad. Sci. USA 88: 10421-10425 and McNellis et al. (1998) Plant J. 14 (2): 247-257), ethanol-inducible and tetracycline-inducible promoters (see, for example, Gatz et al. (1991) Mol. Gen. Genet. 227: 229-237; U.S. Pat. Nos. 5,814,618 and 5,789,156).

The person skilled in the art knows that the use of inducible promoters allows the production of plants, or plant cells, which express only transiently the sequences according to the invention. Such transient expression allows the production of plants which only exhibit transient pathogen resistance. Such transient resistance can be desirable, for example, when the risk of a pathogen contamination is looming, and the plants therefore need to be resistant to the pathogen for only a certain period. Additional situations, in which a transient resistance is desirable, are known to the person skilled in the art. Furthermore, the person skilled in the art also knows that transient expression, and thereby transient resistance can be achieved by the use of vectors non-stably replicating in plant cells, and carrying the respective sequences for the expression of the peroxidase.

Tissue-specific promoters can also be used in order to achieve increased peroxidase expression within a certain plant tissue. Suitable tissue-specific promoters are, for instance, those allowing leaf-specific expression. These include those described in Yamamoto et al. (1997) Plant J. 1 (2): 255-265; Kwon et al. (1994) Plant Physiol 105: 357-367; Yamamoto et al. (1994) Plant Cell Physiol. 35 (5): 773-778; Gotor et al. (1993) Plant J. 3: 509-518; Orozco et al. (1993) Plant Mol. Biol. 23 (6): 1129-1138: Matsuoka et al. (1993) Proc. Natl. Acad. Sci. USA 90 (20): 9586-9590; Stockhaus et al. (1987) Proc. Natl. Acad. G. USA 84: 7943-7947; Stockhaus et al. (1989) EMBO J. 8: 2445-2451.

The use of epidermis-specific promoters is also particularly preferred, since the task of the epidermis as the outer tissue of the overground organs of higher plants is among other things to prevent pathogens from penetrating into the plant. Suitable epidermis-specific promoters include, among others, the promoter of the CER6 (CUT1) gene of *Arabidopsis* (Hooker et al. (2002) Plant Physiol. 129 (4): 1568-1580 and Kunst et al. (2000) Biochem. Soc. Trans. 28 (6): 651-654).

Other preferred promoters are those that are especially active in fruit. These include, for example, the promoter of a polygalacturonase gene, e.g. of the tomato (Nicholass et al. (1995) Plant Mol. Biol. 28:423-435), the promoter of an ACC oxidase, e.g. of apple (Atkinson et al. (1998) Plant Mol. Biol. 38:449-460), or the 2A11 promoter of tomato (van Haaren et al. (1991) Plant Mol. Biol. 17:615-630).

Also preferred are mesophyll-specific promoters, such as the rbcs promoter of rice or tomato (Kyozuka et al. (1993) Plant Physiol. 102 (3): 991-1000), the PPCZm1 promoter of corn (Kausch et al. (2001) Plant Mol. Biol. 45 (1): 1-15), the CAB2 promoter of *Arabidopsis* (Thain et al. (2002) Plant Physiol. 130: 102-110), or the AldP promoter of rice (Kagaya et al. (1995) Mol Gen Genet. 248 (6): 668-674).

Furthermore, the person of average skilled in the art is able to isolate additional suitable promoters using routine methods. Thus, the person skilled in the art using current molecular biological methods, such as hybridization experiments, or DNA protein binding studies is able to identify e.g. additional epidermis-specific regulatory nucleic acid elements. Here, for example, the desired tissue is isolated in a first step from the desired organism from which the regulatory sequences are to be isolated, the entire poly(A)$^+$ RNA is isolated from it, and a cDNA library is created. In a second step, using cDNA clones which are based on poly(A)$^+$ RNA molecules from another tissue, those clones are identified from the first bank by means of hybridization whose corresponding poly(A)$^+$ RNA molecules merely accumulate in the desired tissue. Then, using the cDNAs thus identified, promoters are isolated which have tissue-specific regulatory elements. Additional PCR based methods for the isolation of suitable tissue-specific promoters are also available to the person skilled in the art.

The vectors according to the invention, as the regulatory elements, can additionally comprise, e.g. enhancer elements. They may also contain resistance genes, replication signals, and additional DNA regions, which enable propagation of the vectors in bacteria, such as *E. coli*. The regulatory elements also comprise sequences which effect a stabilization of the vectors in the host cells. Such regulatory elements particularly comprise sequences facilitating stable integration of the vector into the host genome of the plant, or an autonomous replication of the vector in the plant cells. Such regulatory elements are known to the person skilled in the art.

The so-called termination sequences are sequences which ensure the proper termination of transcription, or translation. If the transferred nucleic acids are to be translated, the termination sequences are typically stop codons and respective regulatory sequences; if the transferred nucleic acids are only to be transcribed, they are generally poly(A) sequences.

As used herein, the term "vector" relates to a nucleic acid molecule which can transport another nucleic acid, to which it is bound, into a cell. A vector type is a "plasmid" representing a circular double stranded DNA loop, into which additional DNA segments can be ligated. Another vector type is a viral vector, wherein additional DNA segments can be ligated into the viral genome. Certain vectors can replicate autonomously in a host cell into which they have been inserted (e.g. bacterial vectors with a bacterial replication origin). Other vectors are advantageously integrated into the genome of a host cell when inserted in the host cell, and thereby replicated together with the host genome. Also, certain vectors can control the expression of genes to which they are functionally linked. These vectors are called here "expression vectors." Usually, expression vectors suitable for DNA recombination techniques are of the plasmid type. In the present description "plasmid" and "vector" can be used interchangeably, since the plasmid is the vector type most often used. However, the invention is also intended to comprise other types of expression vectors, such as viral vectors which fulfil similar functions. Furthermore, the term "vector" is also intended to comprise other vectors known to the person skilled in the art, such as phages, viruses, such as SV40, CMV, TMV, transposons, IS elements, phasmids, phagemids, cosmids, linear or circular DNA.

In a recombinant expression vector, the term "operatively linked thereto" means that the nucleotide sequence of interest is linked to the regulatory sequence(s) in such a way that the expression of the nucleotide sequence is possible, and that both sequences are linked to each other in such a way so as to fulfil the predicted function ascribed to the sequence.

The term "regulatory sequence" is intended to comprise promoters, enhancers, and other expression control elements (e.g. polyadenylation signals). These regulation sequences are described e.g. in Goeddel: Gene Expression Technology: Methods in Enzymology 185, Academic Press, San Diego, Calif. (1990), or in Gruber and Crosby, in: Methods in Plant Molecular Biology and Biotechnology, CRC Press, Boca Raton, Fla., publisher: Glick and Thompson, Chapter 7, 89-108. Regulatory sequences comprise those sequences which regulate the constitutive expression of a nucleotide sequence in many types of host cells, and those sequences which regulate the direct expression of the nucleotide sequence only in certain host cells under certain conditions. The person skilled in the art knows that the design of the expression vector can depend on factors, such as the choice of the host cell to be transformed, the desired extent of the protein expression, etc.

The recombinant expression vectors used for the expression of the peroxidase can be active in both prokaryotic and eukaryotic cells. This is advantageous, since intermediate steps of the vector construction are often performed for the sake of simplicity in microorganisms. These cloning vectors contain a replication signal for the respective microorganism, and a marker gene for the selection of successfully transformed bacterial cells. Suitable vectors for expression in prokaryotic organisms are known to the person skilled in the art; they include e.g. *E. coli* pLG338, pACYC184, the pBR series, such as pBR322, the pUC series, such as pUC18, or pUC19, the M113 mp series, pKC30, pRep4, pHS1, pHS2, pPLc236, pMBL24, pLG200, pUR290, pIN-III1113-B1, λgt11, or pBdCl, *Streptomyces* pIJ101, pIJ364, pIJ702, or pIJ361, *Bacillus* pUB110, pC194, or pBD214, *Corynebacterium* pSA77, or pAJ667.

In another embodiment the expression vector represents a yeast expression vector or a bacillovirus expression vector.

The above named vectors provide only a small overview of possible suitable vectors. Additional plasmids are known to the person skilled in the art and are described in e.g.: Cloning Vectors (publisher Pouwels, P. H. et al. Elsevier, Amsterdam, New York-Oxford, 1985). For additional suitable expression systems for prokaryotic and eukaryotic cells see chapters 15 and 16 of Sambrook and Russell, vide supra.

In another embodiment of the method, the peroxidase can be expressed in single-celled plant cells (such as algae), see Falciatore et al., 1999, Marine Biotechnology 1 (3):239-251 and the literature cited therein, and in plant cells of higher plants (e.g. spermatophytes, such as crop plants). Examples for plant expression vectors comprise those extensively described in: Becker, D., Kemper, E., Schell, J., and Masterson, R. (1992), Plant Mol. Biol. 20:1195-1197; and Bevan, M. W. (1984), Nucl. Acids Res. 12:8711-8721; Vectors for Gene Transfer in Higher Plants; in: Transgenic Plants, Bd. 1, Engineering and Utilization, publisher: Kung and R. Wu, Academic Press, 1993, S. 15-38.

Since the expression of plant genes is frequently not limited to the transcription level, a plant expression cassette preferably contains, in addition to the elements described above, other functionally linked sequences such as translation enhancers, e.g. the overdrive sequence containing the 5' untranslated leader sequence of the tobacco mosaic virus, which increases the protein/RNA ratio (Gallie et al. (1987) Nucl. Acids Research 15:8693-8711).

The gene to be expressed must, as described above, be functionally linked to a suitable promoter which regulates the gene expression in a time specific, cell specific or tissue specific manner. Suitable promoters have already been described above.

Other preferred sequences for the use in the functional connection in gene expression cassettes are targeting sequences which are required for the targeting of the gene product into the respective cell compartment (see an overview in Kermode (1996) Crit. Rev. Plant Sci. 15 (4): 285-423 and the literature cited therein), such as into the vacuole, the nucleus, all types of plastids, such as amyloplasts, chloroplasts, chromoplasts, the extracellular space, the mitochondria, the endoplasmatic reticulum, elaiosomes, peroxisomes, and other compartments of plant cells.

In order to insert the peroxidase sequences into the expression vectors, they are advantageously subjected to an amplification and ligation in the known manner. Preferably, one proceeds in accordance with the protocol of the Pfu DNA polymerase, or a Pfu/Taq DNA polymerase mixture. The primers are selected in accordance with the sequence to be amplified. Advantageously, the primer should be selected so that the amplificate comprises the entire codogenic sequence from the start codon to the stop codon. Advantageously, the amplificate is analyzed subsequent to the amplification. For example, the analysis can be made in respect of quality and quantity after gel electrophoretic separation. The amplificate can then be purified according to a standard protocol (e.g. Qiagen). An aliquot of the purified amplificate is then available for the subsequent cloning.

Suitable cloning vectors are generally known to the person skilled in the art. These particularly include vectors which are replicable in microbial systems, i.e. especially vectors which allow for an efficient cloning in bacteria, yeasts or fungi, and which allow for the stable transformation of plants. Especially worth mentioning are various binary and co-integrated vector systems suitable for the T-DNA mediated transformation. Such vector systems are usually characterized in that they contain at least the vir-genes needed for the *agrobacteria* mediated transformation, as well as the T-DNA limiting sequences (T-DNA border). Preferably, these vector systems also comprise further cis regulatory regions, such as promoters and terminators and/or selection markers used to identify the respective transformed organisms. While vir genes and T-DNA sequences are arranged on the same vector in co-integrated vector systems, binary systems are based on at least two vectors, one of which carries vir genes, but no T-DNA, and a second carries T-DNA, but no vir genes. The latter vectors are thus relatively small, easy to manipulate and replicable both in *E. coli* as well as in *agrobacterium*. These binary vectors include vectors of the series pBIB-HYG, pPZP, pBecks, pGreen. According to the invention, Bin19, pBI101, pBinAR, pGPTV and pCAMBIA are preferred. An overview of binary vectors and their use is provided by Hellens et al. (2000) Trends in Plant Science 5, 446-451.

For the preparation of the vector, the vectors can initially be linearized by means of restriction endonuclease(s) and then enzymatically modified in any suitable way. The vector is then purified and an aliquot is used for cloning. During cloning the enzymatically cut and if necessary purified amplificate is linked to similarly prepared vector fragments by means of a ligase. A certain nucleic acid construct, or vector construct, or plasmid construct, may have one, or even several, codogenic gene regions. Preferably, the codogenic gene regions in these constructs are functionally linked to regulatory sequences. The regulatory sequences especially include plant sequences, such as the promoters and terminators described above. The constructs can be advantageously cultivated in microorganisms, especially in *E. coli* and *Agrobacterium tumefaciens*, in a suitable medium, and stably propagated under selection conditions. The cells are then harvested and lysed and the plasmid is extracted therefrom. This allows a transfer of heterologous DNA into plants or microorganisms.

With the advantageous use of cloning vectors, the nucleic acids used in the method according to the invention, the nucleic acids and the nucleic acid constructs according to the invention can be inserted into organisms, such as microorganisms, or preferably plants, and used for plant transformation, just as those published and cited in: Plant Molecular Biology and Biotechnology (CRC Press, Boca Raton, Fla.), Chapters 6/7, p. 71-119 (1993); F. F. White, Vectors for Gene Transfer in Higher Plants; in: Transgenic Plants, Bd. 1, Engineering and Utilization, publisher: Kung and R. Wu, Academic Press, 1993, 15-38; B. Jenes et al., Techniques for Gene Transfer, in: Transgenic Plants, Bd. 1, Engineering and Utilization, publisher: Kung and R. Wu, Academic Press (1993), 128-143; Potrykus (1991) Annu. Rev. Plant Physiol. Plant Molec. Biol. 42: 205-225. The nucleic acids used in the method, the nucleic acids and nucleic acid constructs, and/or vectors according to the invention, can therefore be used for the genetic modification of a broad spectrum of organisms, preferably of plants.

There are plurality of known techniques available for inserting DNA into a plant host cell, and the person skilled in the art will have no difficulty in finding the most suitable method in each case. These techniques comprise the transformation of plant cells with T-DNA using *Agrobacterium tumefaciens* or *Agrobacterium rhizogenes* as transformation agent, the fusion of protoplasts, the direct gene transfer of isolated DNA into protoplasts, the electroporation of DNA, the insertion of DNA by means of the biolistic method, as well as other possibilities. Both stable and transient transformants can be generated in this manner.

For injection and electroporation of DNA in plant cells there are no special demands made per se on the plasmids used. Similar is true for the direct gene transfer. Simple plasmids such as pUC derivatives can be used. However, if whole plants are to be regenerated from such transformed cells, the presence of a selectable marker gene is necessary. The person skilled in the art knows the most commonly used selection markers, and selecting a suitable marker does not present a problem to him. Commonly used selection markers are those which make the transformed plant cells resistant to a biocide or to an antibiotic, such as kanamycin, G418, bleomycin, hygromycin, methotrexate, glyphosate, streptomycin, sulfonylurea, gentamycin, or phosphinotricin the like. The individually selected marker should allow the selection of transformed cells as opposed to cells lacking the inserted DNA. For this purpose, alternative markers, such as nutrition markers or screening markers (such as GFP, green fluorescent protein) are also suitable. Of course, selection markers may also be completely dispensed with, which however, greatly increases the need for screening. If marker-free transgenic plants are desired, strategies are also available to the person skilled in the art which allow subsequent removal of the marker gene, such as the cotransformation, or sequence-specific recombinases. Once the inserted DNA has been integrated into the genome of the plant cell, it is usually stable there, and will also remain in the progeny of the originally transformed cell.

If *agrobacteria* are used for the transformations, the DNA to be inserted must be cloned into special plasmids, as explained above, either in an intermediary or in a binary vector. The intermediary vectors can, due to sequences which are homologous to the sequences in the T-DNA, be integrated in the Ti or Ri plasmid of the *agrobacteria* by means of homologous recombination. The plasmid also contains the vir region necessary for the transfer of the T-DNA. Intermediary vectors are unable to replicate in *agrobacteria*. The intermediary vector can be transferred to *Agrobacterium tumefaciens* by means of a helper plasmid (conjugation). Binary vectors can replicate both in *E. coli*, as well as in *agrobacteria*. They contain a selection marker gene and a linker or polylinker, which are framed by the right and the left T-DNA boundary region. They can be transformed into the *agrobacteria* directly (Holsters et al. (1978), Molecular and General Genetics 163, 181-187). The *agrobacterium* serving as the host cell should contain a plasmid carrying a vir region. The vir region is necessary for the transfer of the T-DNA into the plant cell. T-DNA may also be present. The *agrobacterium* transformed in this way is used for the transformation of plant cells.

The use of T-DNA for the transformation of plant cells has been extensively analyzed, and sufficiently described in EP 120 515.

For the transfer of the DNA into the plant cell, plant explants can advantageously be cultivated with *Agrobacterium tumefaciens* or *Agrobacterium rhizogenes*. Whole plants can then be regenerated from the infected plant material (such as leaf sections, stalk segments, roots, but also protoplasts or suspension-cultivated plant cells) in a suitable medium, which may contain antibiotics or biozides for the selection of transformed cells. The regeneration of the plants is performed according to conventional regeneration methods using known culture media. The plants, or plant cells, obtained in this manner can then be analyzed for the presence of inserted DNA by means of established methods, such as Southern Blot or PCR.

Other possibilities for inserting foreign DNA using the biolistic method or by protoplast transformation are known to the person skilled in the art (see L. Willmitzer (1993) Transgenic Plants in: Biotechnology, A Multi-Volume Comprehensive Treatise (publisher: H. J. Rehm et al.), Volume 2, 627-659, VCH Weinheim, Germany).

Meanwhile not only has the transformation of dicotyledonous plants, or their cells, become well established via Ti plasmid vector systems by means of *Agrobacterium tumefaciens*, but also the one of monocotyledonous plants, or their cells (see, among others, Chan et al. (1993), Plant Mol. Biol. 22, 491-506).

Alternative systems for the transformation of monocotyledonous plants, or their cells, include the transformation by means of the biolistic approach (Wan and Lemaux (1994) Plant Physiol. 104, 37-48; Vasil et al. (1993) Bio/Technology 11, 1553-1558; Ritala et al. (1994) Plant Mol. Biol. 24, 317-325; Spencer et al. (1990), Theor. Appl. Genet. 79, 625-631), protoplast transformation, electroporation of partially permeabilized cells, as well as the insertion of DNA by means of fiber glass.

The transformed cells grow within the plant in the usual way (also see McCormick et al. (1986), Plant Cell Reports 5, 81-84). The resulting plants can be cultivated normally, and interbred with plants having the same transformed genetic code, or a different genetic code. The resulting hybrid individuals possess the corresponding phenotypical characteristics.

Two or more generations should be cultivated in order to ensure that the phenotypical characteristic is stably retained and transmitted. Also, seeds should be harvested in order to ensure that the respective phenotype, or other characteristic have been retained.

Likewise, transgenic lines can be identified according to conventional methods which lines are homozygous for the new nucleic acid molecules, and their phenotypical behavior with regard to a present, or absent pathogen responsiveness can be analyzed and compared to the behaviour of hemizygous lines.

Of course, the plant cells containing the nucleic acid molecules according to the invention may also be further cultivated in the form of a cell culture (including protoplasts, calli, suspension cultures, and the like).

The method according to the invention can advantageously be combined with additional methods which confer pathogen resistance (for instance against insects, fungi, bacteria, nematodes, etc.), stress resistance, or another improvement of plant characteristics. Examples are mentioned, inter alia, in Dunwell J M (2000) J Exp Bot. 51: 487-496.

According to the invention, the term transgenic plant comprises the plant in its entirety, as well as all parts of the plant in which the expression of plant peroxidase proteins according to the invention is increased. This includes all parts of the plant and plant organs, such as leaf, stem, seed, root, tubers, anthers, fibers, root hair, stalk, embryos, calli, cotelydons, petioles, crop material, plant tissue, reproductive tissue, cell cultures derived from the transgenic plant, and/or which can be used to produce the transgenic plant.

Depending on the vector system used, transgenic plants can also be generated according to the invention, in which the nucleic acids to be transferred are contained in the plant cell, or the plant, as an independently replicating system. The vectors used for the transfer of the plants must then possess the corresponding DNA sequences which facilitate the replication of the plasmids used for the transfer within the cell.

The specific expression of the peroxidase protein in the plants, or plant cells, according to the invention can be proven and tracked by means of common molecular biological and biochemical methods. The person skilled in the art knows these techniques and is easily able to select suitable detection methods, such as a Northern Blot analysis for the detection of peroxidase-specific RNA, or for the determination of the amount of accumulation of peroxidase-specific RNA, or a Southern Blot, or PCR, analysis for the detection of DNA sequences encoding the peroxidase. The probe or primer sequences used for this purpose can either be identical to the sequences given in SEQ ID No. 1, or 3, or show some slight differences to these sequences.

Of course, the techniques described above may also be used to identify additional plants having a non-host resistance due to the presence of the peroxidase identified in the present invention.

The plants used for the method according to the invention can in principle be any plant which is to be made resistant to a pathogen infestation. Preferably, it is a monocotyledonous or dicotyledonous agricultural plant, a food plant or a fodder plant.

Examples pf monocotyledonous plants are plants belonging to the genera *Avena* (oat), *Triticum* (wheat), *Secale* (rye), *Hordeum* (barley), *Oryza* (rice), *Panicum*, *Pennisetum*, *Setaria*, *Sorghum* (millet), *Zea* (corn), and the like.

Dicotyledonous agricultural plants comprise, inter alia, cotton, leguminous plants such as pulses, and especially alfalfa, soy bean, oilseed rape. canola, tomato, sugar beet, potato, sunflower, ornamental plants as well as trees. Additional agricultural plants can comprise fruit (especially apples, pears, cherries, grapes, citrus, pineapples, and bananas), oil palms, tea, cocoa and coffee bushes, tobacco, sisal as well as in medical plants Rauwolfia and Digitalis. Especially preferred are the cereals wheat, rye, oats, barley, rice, corn, and millet, as well as the dicotyledonous plants sugar beet, oilseed rape, soy, tomato, potato, and tobacco. Additional agricultural plants can be gathered from U.S. Pat. No. 6,137,030.

Preferred plants are marigold, sunflower, *Arabidopsis*, tobacco, red pepper, soy, tomato, eggplant, peppers, carrot, potato, corn, lettuce and types of cabbage, cereals, alfalfa, oats, barley, rye, wheat, triticale, millet, rice, alfalfa, flax, cotton, hemp, *Brassicacaes*, such as oilseed rape or canola, sugar beet, sugarcane, nut and wine species, or trees, such as aspen or yew tree.

A further object of the invention relates to the use of the transgenic plant according to the invention and the cells, cell cultures, parts and transgenic reproduction materials derived from it for the production of food and fodder, pharmaceuticals or fine chemicals.

The identification of the peroxidase from barley as a gene mediating non-host resistance of barley to isolates of *Blumeria graminis* f. sp. *triticum* as well as its use for mediating the pathogen resistance in transgenic plants, or plant cells, respectively, will now be explained below. The following examples should not be construed as limiting. The content of all literature, patent applications, patents, and published patent applications cited in this patent application is incorporated herein by reference.

EXAMPLES

Example 1

General Cloning Methods

The cloning methods, such as restriction digests, agarose gel electrophoresis, purification of DNA fragments, transfer of nucleic acids to nitrocellulose and nylon membranes, linking of DNA fragments, transformation of *E. coli* cells, cultivation of bacteria, and sequence analysis of recombinant DNA were performed as described by Sambrook et al. (2001), vide supra.

Example 2

Sequence Analysis of Recombinant DNA

The sequencing of recombinant DNA molecules was performed using a laser fluorescence DNA sequencer of ABI according to the method by Sanger (Sanger et al. (1977) Proc. Natl. Acad. Sci. USA 74, 5463-5467).

Example 3

Identification of HvBgt1 of Barley by means of Oligonucleotide Fingerprinting

The peroxidase gene HvBgt1 of barley was identified by means of oligonucleotide fingerprinting (Radelof et al. (1998) Nucleic Acids Res. 26(23):5358-64) as a Bgt-induced gene. This method allows identification of expression patterns even of very low expressed genes.

HvBgt1 was identified in a library generated from mRNA of barley plants which had been infected with wheat mildew (Bgt; harvest times of leaf tissue: 6, 24, 48 and 72 h.p.i.). Using the software HyStac developed by the BASF Corporation, the abundance of the individual clusters in this library was compared to the abundance of two additional barley libraries (barley inoculated with barley mildew (Bgh) as well as non-inoculated barley) which served as reference. For HvBgt1 this analysis indicated an abundance increased by approximately 10 times in the barley+Bgt library.

Example 4

Culture of the Barley Lines and Infection with Mildew

The barley wild type line Ingrid MLOBc was used for the experiments. The seeds were provided by Dr. Patrick Schweizer, IPK Gatersleben.

After placing on soil the seeds were incubated for 24 hrs at 4° C. for the purpose of stratification. The plants were then placed in the greenhouse (Agrarzentrum Limburgerhof, BASF AG) at controlled growth conditions. The mean temperature was 23° C.; the humidity was between 40 and 70%. The day/night rhythm was 10 hrs and 14 hrs, respectively. 7 days after sowing, the plants were inoculated with Bgh or Bgt. The isolate FA6h of the pathogen *Blumeria graminis* f. sp. *hordei* used for the experiments was provided by the research station of the ETH Zurich at Heckenholz. The pathogen *Blumeria graminis* f. sp. *tritici* is a field isolate cultivated at the Agrarzentrum of BASF AG on the wheat variety Kanzler. For the infection, barley plants which were severely infected with Bgh, or wheat plants which were severely infected with Bgt, respectively, were held over the barley, or *Arabidopsis* plants to be infected, and the mildew shaken off in order to transfer the conidia to the plant.

Example 5

Isolation of the Total RNA of Infected Barley Plants

Over a period of four days, infected barley material and non-infected controls were harvested at intervals of 24 hours, wrapped in aluminum foil and deep-frozen in dry ice. The storage of the leaf material occurred at −80° C. After breaking up the leaf material into small pieces, the total RNA was isolated with the aid of the RNeasy Plant Maxi Kit® (Qiagen, Hilden, Germany) according to the manufacturer's instructions. The elution of the purified RNA was performed with 2×0.6 ml of RNase-free water. The concentration was determined using the EPPENDORF BioPhotometer 6131, and subsequently the RNA was precipitated with 2 volume parts of 98% ethanol and 1/10 volume parts of Na acetate (3 M, pH 5.2), and adjusted to a concentration of approximately 2 µg/µl.

Example 6

Determining the peroxidase expression by means of quantitative PCR analyses

The RNA samples isolated from the leaf material were used for the quantitative PCR. At first, any DNA still remaining in the RNA samples was digested. The digest was prepared with DNA-free™ from AMBION (Huntingdon, USA) as follows:

| | |
|---|---|
| RNA | 50 µl |
| 10x DNase I buffer | 6 µl |
| DNase I (2 U/µl) | 2 µl |
| H$_2$O ad 60 µl | 2 µl |

The mixture was incubated for 30 min at 37° C. 9 µl of DNase inactivation reagent was then added and the solution mixed well. After an additional incubation time of 2 min at room temperature, the solution was centrifuged at 10,000 g for 1 min in order to pellet the DNase inactivation reagent. The RNA was transferred into a new vessel and stored at −20° C.

After the DNase digest, the RNA was reversely transcribed in cDNA. The assay was performed using the Taq Man Reverse Transcription Reagents from APPLIED BIOSYSTEMS (Applera Deutschland GmbH, Darmstadt, Germany):

| | |
|---|---|
| RNA | 6 µl |
| 25 mM MgCl$_2$ | 4.4 µl |
| dNTP-Mix (10 mM) | 4 µl |
| 50 µM random hexamer | 1 µl |
| 10x RT buffer | 2 µl |
| RNase inhibitor | 0.4 µl |
| Multiscribe RT (50 U/µl) | 1.5 µl |
| H$_2$O nuclease-free | 0.7 µl |

The mixture was incubated for 10 min at 25° C., and then at 37° C. for 60 min. Finally, the mixture was heat-inactivated for 5 min at 95° C.

The transcribed DNA was diluted with 20 µl of H$_2$O and 2.5 µl thereof was used for the quantitative PCR. The 18S rRNA was determined as the internal standard. A triple determination was performed for all samples. The mixtures were pipetted into a 96 well plate. At first the cDNA was pipetted individually, then the SYBR Greene® Master Mix was separately added with the primers and the corresponding amount of water, and the solution was mixed.

| | |
|---|---|
| cDNA | 2.5 µl |
| 2x SYBR Green ® Master Mix | 12.5 µl |
| forward primer, Gip 162, 200 nM | 0.09 µl |
| reverse primer, Gip 163, 200 nM | 0.14 µl |
| H$_2$O nuclease-free ad 25 µl | 9.77 µl |
| Gip 162: CGAGGCCCTTGTGACATACAT | (SEQ ID NO: 7) |
| Gip 163: ACTTAGGTGTCGTTACTTGGACCAT | (SEQ ID NO: 8) |

The respective control value before infection served as a reference sample (0 hrs). Determination of the transcript amount took place with samples which were taken 24 hrs, 48 hrs and 72 hrs after infection with Bgh.

Setup for the 18S rRNA:

| | |
|---|---|
| cDNA | 2.5 µl |
| 2x SYBR Green ® Master Mix | 12.5 µl |
| forward primer, Gip 63, 200 nM | 0.12 µl |
| reverse primer, Gip 64, 200 nM | 0.13 µl |
| H$_2$O nuclease-free | 9.75 µl |
| Gip 63: CGTCCCTGCCCTTTGTACAC | (SEQ ID NO: 9) |
| Gip 64: AACACTTCACCGGACCATTCA | (SEQ ID NO: 10) |

The plate was centrifuged at room temperature and 2,500 rpm for 1 min and the samples were measured directly in the ABI PRISM 7000 device from APPLIED BIOSYSTEMS (Applera Deutschland GmbH, Darmstadt, Germany). Evaluation was carried out using the program ABI PRISM 7000 SDS of the company APPLIED BIOSYSTEMS.

The expression data determined using the quantitative PCR are illustrated in Table 5 and FIG. 1. The measurement was performed twice and a triple determination of the individual measurement values done. Shown are the respective mean values as well as the related standard deviation.

TABLE 5

Illustration of the chronological course of the expression of HvBgt1 in non-host (barley and Bgt) and host interaction (barley with Bgh)

| Sample No. | Plant material | | Gene expression | Standard deviation | Calibrator |
|---|---|---|---|---|---|
| 1 | Ingrid Kont. | 0 hrs | 1.0 | 0.1 | Ingrid |
| 2 | Ingrid Kont. | 24 hrs | 6.1 | 3.5 | 0 h control |
| 3 | Ingrid Kont. | 48 hrs | 28.2 | 4.9 | |
| 4 | Ingrid Kont. | 72 hrs | 25.1 | 3.4 | |
| 5 | Ingrid + Bgt | 0 hpi | 1.0 | 0.3 | Ingrid + Bgt |
| 6 | Ingrid + Bgt | 24 hpi | 107.1 | 18.3 | 0 hpi |
| 7 | Ingrid + Bgt | 48 hpi | 25.0 | 12.9 | |
| 8 | Ingrid + Bgt | 72 hpi | 10.6 | 5.0 | |
| 9 | Ingrid + Bgh | 0 hpi | 1.0 | 0.1 | Ingrid + Bgh |
| 10 | Ingrid + Bgh | 24 hpi | 1.5 | 0.6 | 0 hpi |
| 11 | Ingrid + Bgh | 48 hpi | 0.5 | 0.1 | |
| 12 | Ingrid + Bgh | 72 hpi | 3.1 | 1.2 | |

The 0 hrs value of the measurement served as the comparative value, or calibrator, for each interaction.

The results show a significant difference in the HvBgt1 expression between the three systems control, non-host interaction and host interaction. A significant increase in the transcription amount of about 28 times is recorded in the control up to the time of 48 hrs, which then remains almost constant up to 72 hrs after the start of the measurement. In the non-host interaction (barley Bgt) on the other hand, an increase of almost 110 times is perceived after 24 hrs, which then slowly drops to 10 times the amount after 72 hrs. In contrast, an increase of the transcription amount of only three times maximum over the entire time is perceived in the host interaction (barley Bgh).

Example 7

Isolation of the Full Length Sequence of HvBgt1 of Barley via RACE-PCR

The RNA isolated from the infected leaf material was used for the RACE-PCR. The RACE cDNA library was generated with the GeneRacer™-Kit from Invitrogen (Karlsruhe, Germany) according to the manufacturer's instructions. As gene-specific primers (GSP) the primer M207 was used as the 5' RACE primer, and primer M208 was used as the nested primer.

M207: GCTTATTCAGCAGCCAACAAAGTAAC (SEQ ID NO: 11)

M208: CTGTTTCACAAGTTTATGGTCCAAGTAA (SEQ ID NO: 12)

Set-up of the sample PCR:

| | |
|---|---|
| 10x polymerase buffer | 5 µl |
| dNTP Mix (10 mM), INVITROGEN | 1.5 µl |
| Template (Hv-RACE library) | 1 µl |
| GSP, M 207 (10 pmol) | 4 µl |
| GeneRacer X'Primer (10 pmol) | 4.5 µl |
| Polymerase (5 U/µl) | 1 µl |
| H₂O | 33 µl |

PCR Program

| | | |
|---|---|---|
| Denaturation | 95° C. | 2 min |
| Denaturation | 95° C. | 30 sec |
| Annealing | 65° C. | 30 sec |
| Elongation | 68° C. | 2 min |
| Final Elongation | 68° C. | 10 min |

25x (for Denaturation, Annealing, Elongation)

Set-up for the sample-nested PCR:

| | |
|---|---|
| 10x polymerase buffer | 5 µl |
| dNTP Mix (10 mM), INVITROGEN | 1.5 µl |
| Template (PCR set-up) | 5 µl |
| GSP, M 207 (10 pmol) | 4 µl |
| GeneRacer X' nested primer, M 208 (10 pmol) | 4.5 µl |
| Polymerase (5 U/µl) | 1 µl |
| H₂O | 33 µl |

PCR Program

| | | |
|---|---|---|
| Denaturation | 95° C. | 2 min |
| Denaturation | 95° C. | 30 sec |
| Annealing | 65° C. | 30 sec |
| Elongation | 68° C. | 2 min |
| Final Elongation | 68° C. | 10 min |

25x (for Denaturation, Annealing, Elongation)

The full length sequence of the gene HvBgt1 was amplified in several partial steps, subsequently sequenced, and then assembled in silico. Having amplified one part of the sequence with poly-A extension via 3' RACE and another part of the sequence via 5'RACE, the new sequences could be conjugated with the original sequence via a Contig. The entire sequence was approximately 1,000 bp. All possible ORFs in the sequence were displayed by means of the computer program ContigExpress (INFORMAX, Maryland, USA). An ORF was found which extends across the length of 945 bp. In order to verify whether the gene was complete, an additional stop codon was searched for upstream of the start. The stop codon was found after 3 triplets in 5' direction.

In order to obtain the gene as a full length clone, primers were selected which allow the amplification of the entire gene (end-to-end PCR). The PCR fragment was then purified from the agarose gel, and cloned into the pCR®4-TOPO® vector. The full length nucleotide sequence of HvBgt1 is illustrated in SEQ ID No. 1, and the amino acid sequence is illustrated in SEQ ID No. 2.

Example 8

Identification and cloning of the Genes Homologous to HvBgt1 in *Arabidopsis thaliana*

After the full length sequence of the barley peroxidase (HvBgt1) had been obtained, a BLAST search for the *Arabidopsis* genome was performed with this sequence. Two homologous genes, AtBgt1-1 and AtBgt1-2, were identified. These two genes were amplified by means of PCR with suitable primers from *A. thaliana* cDNA, and cloned into the plant expression vector pCambia with a constitutive promoter in order to facilitate an overexpression in *A. thaliana*.

First, the total RNA was transcribed in cDNA from a mixture of non-infected *Arabidopsis plants* and *Arabidopsis* plants which had been infected with *Alternaria alternata* and *Alternaria brassicola*, using the Superscript First Strand Synthesis System for RT-PCR® (INVITROGEN, Karlsruhe, Germany).

In order to amplify the full length sequence of the genes from the cDNA via PCR with platinum Pfx polymerase (INVITROGEN, Karlsruhe, Germany), primers were designed according to the AtBgt1-1, or AtBgt1-2 sequences. The fragment size to be amplified for AtBgt1-2 should be 1015 bp. The amplification of the AtBgt1-2 sequence occurred with the two primers Fra335 and Fra336 according to the following protocol:

| | |
|---|---|
| 10x polymerase buffer, STRATAGENE (La Jolla, USA) | 5 µl |
| dNTP Mix (10 mM), INVITROGEN (Karlsruhe, Germany) | 1 µl |
| cDNA | 1 µl |
| Fra335 (20 pmol) | 1 µl |
| Fra336 (20 pmol) | 1 µl |
| Taq polymerase (5 U/µl) | 1 µl |
| H$_2$O | 40 µl |
| Fra 335: AGAAGTATGTTAAAGGTGGTGTTGTTG | (SEQ ID NO: 5) |
| Fra 336: TGACGAAGAGGTGATTATTGAGC | (SEQ ID NO: 6) |

PCR Program

| | | | |
|---|---|---|---|
| Denaturation | 95° C. | 5 min | |
| Denaturation | 95° C. | 30 sec | |
| Annealing | 55.9° C. | 30 sec | 35x |
| Elongation | 72° C. | 2 min | |
| Final Elongation | 72° C. | 10 min | |

After purification of the PCR fragments from the gel, the sequences were subcloned into the pCR®Blunt-II-TOPO® vector (INVITROGEN, Karlsruhe, Germany), and transformed into TOP10® *E. coli* cells. The colonies containing the construct were selected by means of blue white selection. From these colonies minicultures were inoculated in order to isolate plasmid DNA. Three clones were sequenced (DNA Laboratory, BASF AG, Ludwigshafen, Germany) for each fragment. The clones showed 100% matching sequences, and were cut out of the TOPO® vector with EcoRI and separated by means of gel electrophoresis. The fragments were purified from the gel, and ligated into the vector pCambia, which had been cut with EcoRI.

Example 9

Transient Transformation of Barley Cells, Overexpression and Evaluation of Fungus Pathogen Development Leaf segments of barley cv Pallas were transformed with the HvBgt1-DNA together with a GFP expression vector. The leaves were then inoculated with Bgh and the result analyzed after 48 hrs by means of light and fluorescence microscopy. The penetration of GFP expressing cells was evaluated by means of detection of haustoria in living cells, and by assessment of the fungus development in these same cells. In all six experiments the bombardment of barley cv Pallas by HvBgt1 led to a reduced amount of cells successfully penetrated by Bgh as compared to cells which had been bombarded with a foreign control DNA (humane thyroid hormone receptor, TR).

For the transient transformation of the barley cells a method was used which has already been described for the biolistic insertion of DNA in epidermal cells of barley leaves (Schweizer P et al. (1999) Mol Plant Microbe Interact 12:647-54). Tungsten particles with a diameter of 1.1 µm (particle density 25 mg/ml) were coated with HvBgt1-DNA together with the plasmid DNA of the vector pGFP (GFP under control of the pUBI promoter) as the transformation marker. The following amounts of DNA, or reporter plasmid, were used per shot for the coating: 1 µg pGFP and 2 µg DNA.

For the microcarrier preparation, 55 mg of tungsten particles (M 17, diameter 1.1 µm; Bio-Rad, Munich, Germany) were washed twice with 1 ml of autoclaved distilled water, and once with 1 mL of absolute ethanol, dried and resuspended in 1 ml of 50% glycerol (approximately 50 mg/ml stock solution). The solution was diluted to 25 mg/ml with 50% glycerol, mixed well before use, and suspended in the ultrasonic bath. For the microcarrier coating, 1 µg plasmid, 2 µg HvBgt1 DNA (1 µL), 12.5 µl tungsten particle suspension (25 mg/ml), 12.5 µl 1 M Ca(NO$_3$)$_2$ solution (pH 10) per shot were added together dropwise while continuously stirring, allowed to stand at room temperature for 10 min, briefly centrifuged, and 20 µl removed from the supernatant. The rest containing the tungsten particle was resuspended in the ultrasonic bath and used in the experiment.

For the transformation, segments of barley primary leaves of a length of approximately 4 cm were used. The tissues were placed in Petri dishes (6.5 diameter) on 0.5% phytagar (GibcoBRL™ Life Technologies™, Karlsruhe, Germany) with 20 µg/ml of benzimidazole, and covered at the edges directly before the particle bombardment with a stencil having a rectangular cutout with a dimension of 2.2 cm×2.3 cm. The dishes were placed on the bottom of the vacuum chamber one after another (Schweizer P et al. (1999) Mol Plant Microbe Interact 12:647-54), across which a nylon mesh (mesh width 0.2 mm, Millipore, Eschborn) as diffusor had been inserted on a perforated plate (5 cm over the bottom, 11 cm below the macrocarrier, see below) in order to disperse any particle clumps, and to slow down the particle stream. The macrocarrier affixed on top (plastic sterile filter attachment, 13 mm, Gelman Sciences, Swinney, UK) was loaded with 5.8 µL of DNA-coated tungsten particles (microcarrier, see below) per shot. The pressure in the chamber was reduced by 0.9 bars by means of a membrane vacuum pump (Vacuubrand, Wertheim, Germany), and the tungsten particles were shot onto the surface of the plant tissue with 9 bars of helium gas pressure. The chamber was ventilated immediately thereafter. For labeling of transformed cells, the leaves were shot with the plasmid pGFP (vector on pUC18 basis, CaMV 35S promoter/terminator cassette with the inserted GFP gene; Schweizer P et al. (1999) Mol Plant Microbe Interact 12:647-54; provided by Dr. P. Schweizer, Institute for Plant Genetics (IPK), Gatersleben, Germany). Before each shooting another plasmid, the macrocarrier was thoroughly cleaned with water.

After an incubation time of four hours after bombardment with slightly opened Petri dishes, at room temperature and by daylight, the leaves were inoculated with 100 conidia/mm$^2$ of powdery mildew fungus (*Blumeria graminis* f.sp. *hordei*, race A6), and incubated for additional 36 to 48 hrs under the same conditions before performing the analysis for signs of infection.

The result (e.g. the penetration efficiency, defined as a percentage of attacked cells showing a mature haustorium and a secondary elongating hyphae, was determined by means of fluorescence and light microscopy. Inoculation with 100 conidia/mm$^2$ results in an infestation frequency of approximately 50% of the transformed cells. For every single experiment, a minimum number of 100 interaction areas was evaluated. Transformed (GFP expressing) cells were identified while being stimulated with blue light. Three different categories of transformed cells were identified:

1. Penetrated cells containing a barely recognizable haustorium. A cell with more than one haustorium was evaluated as one cell.
2. Cells which had been attacked by a fungus appressorium, but contained no haustorium. A cell which had been repeatedly attacked by Bgh, but contained no haustorium, was evaluated as one cell.
3. Cells not attacked by Bgh.

Stomatal cells and stomatal secondary cells were excluded for the evaluation. Surface structures of Bgh were analyzed by means of light microscopy, or fluorescence staining of the fungus with 0.1% of calcofluor (w/v in water) for 30 sec. The development of the fungus can be easily evaluated by means of fluorescence microscopy after staining with calcofluor. Although the fungus develops a primary and an appressorial germ tube in HvBGt1-DNA transformed cells, it develops no haustorium. Haustorium development is a prerequisite for the formation of a secondary hyphae.

The relative penetration efficiency (RPE) is calculated as the ratio between the penetration efficiency in cells which had been transformed with HvBgt1 and the penetration efficiency in cells which had been transformed with control DNA. The percent RPE (%-RPE) is calculated as the RPE minus 1 and multiplied by 100.

$$RPE = \frac{[PE \text{ in } HvBgt1 \text{ DNA transformed cells}]}{[PE \text{ in control DNA transformed cells}]}$$

$$\%\text{-}RPE = 100 * (RPE - 1)$$

The %-RPE value (deviation from the average penetration efficiency of the control) serves for determining the susceptibility of cells transfected with HvBgt1 DNA.

In five independent experiments no difference was observed between the transfection with control DNA and water with regard to the penetration efficiency of Bgh.

In order to exclude the possibility of HvBgt1 DNA influencing the transformation rate or the survival rate of the affected cells, the number of the GFP expressing cells was compared between the control experiments and the HvBgt1 DNA experiments. Interestingly, the HvBgt1 overexpression has no influence on the total number, or the number of affected GFP expressing cells.

Example 10

Transformation of *Arabidopsis thaliana* with HvBgt1, and Analysis of Fungus Resistance Wild type *A. thaliana* plants (Columbia) were transformed with the *agrobacterium tumefaciens* strain (EHA105) on the basis of a modified method (Steve Clough and Andrew Bent (1998) Plant J 16(6):735-743) of the vacuum infiltration method according to Bechtold et al. (Bechtold N et al. (1993) CR Acad Sci Paris, Life Sciences 316:1194-1199). A binary expression vector suitable for the *A. tumefaciens* transformation, such as pCambia, was used. Seeds of the *agrobacterium* transformed primary transformants were selected on the basis of the kanamycin resistance. Antibiotic resistant seedlings were planted in soil, and used as fully developed plants for biochemical analysis.

For analyzing the resistance of transgenic *Arabidopsis* plants to pathogenic fungi, inoculations were performed with the biotrophic fungi Peronospora parasitica and *Erysiphe cichoracearum*.

a) *Peronospora* Parasitica 5 to 8 week old plants were sprayed with a conidia spore suspension (approximately 10$^6$ spores/ml). The inoculated plants were covered with a plastic bag and kept dark and moist overnight in a refrigerator at approximately 16° C. After one day, the plastic bag was slightly opened, and later completely removed. Six days after inoculation, the plants were again covered with a plastic bag overnight, which induced sporulation. On the following day, the leaves were examined for the occurrence of conidiophores. Over the next days, the intercellular growth of the fungus led to the induction of weak chloroses right up to strong necroses in the leaves. These symptoms were quantified and tested for significance.

b) *Erysiphe Cichoracearum*

The biotrophic mildew fungus was cultivated on *Arabidopsis* plants. For the infection of the 4-weeks-old transgenic HvBgt1 expressing *Arabidopsis* plants, conidia carriers were removed from the surface of the leaves with a fine brush, and brushed onto the leaves of the transgenic plants. The plants were incubated for 7 days at 20° C. 7 days after inoculation the conidia carriers were visible on the leaves, and chloroses and necroses appeared within the next few days. These symptoms were quantified and tested for significance.

c) Results

The transgenic *Arabidopsis* plants expressing the sense sequences for HvBgt, in most cases show a significantly increased resistance both against *Peronospora* parasitica and against *Erysiphe cichoracearum*, as opposed to the non-transgenic wild type plants.

The transgenic *Arabidopsis* plants expressing the antisense sequences for AtBgt1, or HvBgt1, show significantly increased susceptibility both to *Peronospora* parasitica and to *Erysiphe cichoracearum* as opposed to non-transgenic wild type plants.

Figures

FIG. 1: Illustration of the chronological course of the expression of HvBgt1 in non-host (barley (Ingrid) and Bgt), and in the host interaction (barley (Ingrid) with Bgh)

The relative expression data shown in table 5 is illustrated with the associated standard deviation. The results show the increase of transcript in the non-host interaction during the course of the analysis.

The invention claimed is:

1. A method for the production of transgenic plants or plant cells having increased pathogen resistance, wherein the method comprises inserting into the plants or plant cells a nucleic acid molecule having a DNA sequence selected from the group consisting of:
   i) a DNA sequence comprising the nucleotide sequence as set forth in SEQ ID NO: 1 or SEQ ID NO: 3
   ii) a DNA sequence comprising a nucleotide sequence encoding a protein with the amino acid sequence as set forth in SEQ ID NO: 2 or SEQ ID NO: 4 and
   iii) a DNA sequence having a sequence identity of at least 95% with the nucleotide sequence as set forth in SEQ ID NO: 1 or SEQ ID NO: 3, and expressing the DNA sequence in the transgenic plant or plant cell, wherein the DNA sequence encodes a protein with the activity of a peroxidase.

2. An isolated nucleic acid molecule containing a nucleic acid sequence selected from the group consisting of:
   i) a DNA sequence comprising the nucleotide sequence as set forth in SEQ ID NO: 1,
   ii) a DNA sequence comprising a nucleotide sequence encoding a protein with the amino acid sequence as set forth in SEQ ID NO: 2, and
   iii) a DNA sequence having a sequence identity of at least 95% with the nucleotide sequence as set forth in SEQ ID NO: 1,
   wherein the isolated nucleic acid molecule encodes a protein with the activity of a peroxidase.

3. The nucleic acid molecule according to claim 2, wherein the nucleic acid sequence originates from *Hordeum vulgare*.

4. A recombinant nucleic acid molecule comprising the following elements in 5'-3' orientation:
   regulatory sequences of a promoter active in plant cells,
   operatively linked thereto a DNA sequence,
   optionally, operatively linked thereto regulatory sequences which may serve as transcription, termination and/or polyadenylation signals within the plant cell,
   wherein the DNA sequence is selected from the group consisting of:
   i) a DNA sequence comprising the nucleotide sequence as set forth in SEQ ID NO: 1,
   ii) a DNA sequence comprising a nucleotide sequence encoding a protein with the amino acid sequence as set forth in SEQ ID NO: 2, and
   iii) a DNA sequence having a sequence identity of at least 95% with the nucleotide sequence as set forth in SEQ ID NO: 1,
   and encodes a protein with the activity of a peroxidase.

5. The recombinant nucleic acid molecule according to claim 4, wherein the DNA sequence is expressed under the control of a constitutive promoter.

6. The recombinant nucleic acid molecule according to claim 4, wherein the DNA sequence is expressed under the control of a tissue-specific promoter.

7. The recombinant nucleic acid molecule according to claim 6, wherein the tissue-specific promoter is an epidermis-specific, mesophyll-specific or leaf-specific promoter.

8. The recombinant nucleic acid molecule according to claim 4, wherein the DNA sequence is expressed under the control of an inducible promoter.

9. The recombinant nucleic acid molecule according to claim 8, wherein the inducible promoter is a pathogen-inducible or wound-inducible promoter.

10. The method according to claim 1, comprising the following steps:
    a) producing a recombinant nucleic acid molecule,
    b) transferring the recombinant nucleic acid molecule from step a) into plant cells, and
    c) regenerating plants from the transformed plant cells,
    wherein the recombinant nucleic acid molecule comprises the following elements in 5'-3' orientation:
    regulatory sequences of a promoter active in plant cells,
    operatively linked thereto the DNA sequence, and
    optionally, operatively linked thereto regulatory sequences which may serve as transcription, termination and/or polyadenylation signals within the plant cell.

11. A transgenic plant cell containing a nucleic acid sequence selected from the group consisting of:
    i) a DNA sequence comprising the nucleotide sequence as set forth in SEQ ID NO: 1 or SEQ ID NO: 3,
    ii) a DNA sequence comprising a nucleotide sequence encoding a protein with the amino acid sequence as set forth in SEQ ID NO: 2 or SEQ ID NO: 4, and
    iii) a DNA sequence having a sequence identity of at least 95% with the nucleotide sequence as set forth in SEQ ID NO: 1 or SEQ ID NO: 3,
    wherein the nucleic acid sequence encodes a protein with the activity of a peroxidase, and wherein the transgenic plant cell has an increased pathogen resistance compared to wild-type cells.

12. The transgenic plant cell according to claim 11, wherein the plant cell has an increased content of the protein with the activity of a peroxidase encoded by the nucleic acid sequence as compared to wild-type cells.

13. The transgenic plant cell according to claim 11, which has an increased resistance to mildew, rust and/or *septoria fungi*.

14. The transgenic plant cell according to claim 13, which has an increased resistance to formae speciales of mildew.

15. A transgenic plant or part thereof containing the plant cell according to claim 11.

16. The transgenic plant according to claim 15, wherein the transgenic plant is a monocotyledonous plant selected from the group consisting of the genera of *Arena, Triticum, Secale, Hordeum, Oryza, Panicum, Pennisetum, Setaria, Sorghum*, and *Zea*.

17. The transgenic plant according to claim 15, wherein the transgenic plant is a dicotyledonous plant selected from the group consisting of cotton, alfalfa, soybean, rapeseed, canola, tomato, sugar beet, potato, ornamental plants, sunflower, tobacco, and trees.

18. The recombinant nucleic acid molecule according to claim 4, wherein the DNA sequence is expressed under the control of a 35S CaMV or ubiquitin promoter.

19. The method according to claim 1, wherein the DNA sequence comprises the nucleotide sequence as set forth in SEQ ID NO: 1 or SEQ ID NO: 3, or a nucleotide sequence encoding the amino acid sequence as set forth in SEQ ID NO: 2 or SEQ ID NO: 4.

20. The isolated nucleic acid molecule according to claim 2, wherein the DNA sequence comprises the nucleotide sequence as set forth in SEQ ID NO: 1, or a nucleotide sequence encoding the amino acid sequence as set forth in SEQ ID NO: 2.

21. The recombinant nucleic acid molecule according to claim 4, wherein the DNA sequence comprises the nucleotide sequence as set forth in SEQ ID NO: 1, or a nucleotide sequence encoding the amino acid sequence as set forth in SEQ ID NO: 2.

22. The transgenic plant cell according to claim 11, wherein the nucleic acid sequence comprises the nucleotide sequence as set forth in SEQ ID NO: 1, a nucleotide sequence encoding the amino acid sequence as set forth in SEQ ID NO: 2, or a nucleotide sequence having a sequence identity of at least 95% with the nucleotide sequence as set forth in SEQ ID NO: 1.

23. A transgenic plant or plant cell produced by the method according to claim 1.

24. The transgenic plant or part thereof of claim 15, wherein the part comprises protoplasts, calli, seed, tubers, or cuttings.

25. A transgenic progeny of the transgenic plant of claim 15.

26. The transgenic plant of claim 16, wherein the transgenic plant is selected from the group consisting of oat, wheat, rye, barley, rice, millet and maize.

27. The transgenic plant of claim 15, wherein the transgenic plant is a leguminous plant.

* * * * *